US006454708B1

(12) United States Patent
Ferguson et al.

(10) Patent No.: US 6,454,708 B1
(45) Date of Patent: Sep. 24, 2002

(54) PORTABLE REMOTE PATIENT TELEMONITORING SYSTEM USING A MEMORY CARD OR SMART CARD

(75) Inventors: Pete Ferguson, Cambridge (GB); Harpal Kumar, Cambridge (GB); Graham Lay, Wilburton (GB); Mike Llewellyn, Earith (GB); John D. Place, Bury St. Edmunds (GB)

(73) Assignee: Nexan Limited, Cambridge (GB)

( * ) Notice: Subject to any disclaimer, the term of this patent is extended or adjusted under 35 U.S.C. 154(b) by 118 days.

(21) Appl. No.: 09/591,597

(22) Filed: Jun. 9, 2000

Related U.S. Application Data

(63) Continuation-in-part of application No. 09/292,405, filed on Apr. 15, 1999.

(51) Int. Cl.[7] ................................................ A61B 5/00
(52) U.S. Cl. ..................... 600/300; 128/903; 128/904
(58) Field of Search .................................. 600/300, 301, 600/390, 393, 508, 509; 128/903, 904; 705/1, 2, 3; 607/77

(56) References Cited

U.S. PATENT DOCUMENTS

| 2,298,125 A | 10/1942 | Hartman | 128/2.1 |
|---|---|---|---|
| 2,660,165 A | 11/1953 | Miller | 128/2.06 |

(List continued on next page.)

FOREIGN PATENT DOCUMENTS

| CH | 293560 | 12/1953 |
|---|---|---|
| DE | 195 36 204 A1 | 1/1997 |
| EP | 0 212 278 | 3/1987 |

(List continued on next page.)

OTHER PUBLICATIONS

"Microcomputer–based Telemetry System for ECG Monitoring," *Proceedings of the Ninth Annual Conference of the IEEE Engineering in Medicine and Biology Society*, The Boston Plaza Hotel, Boston, MA, Nov. 13–16, 1987, vol. 3 of 4, 2 pages.

(List continued on next page.)

Primary Examiner—Eric F. Winakur
Assistant Examiner—David McCrosky
(74) Attorney, Agent, or Firm—Woodcock Washburn LLP

(57) ABSTRACT

A system and method for monitoring health parameters and capturing data from a subject. The system is characterized by a cordless, disposable sensor band with sensors for measuring full waveform ECG, full waveform respiration, skin temperature, and motion, and a connector which accepts a memory card or a smart card for storage of the measured data. After a predetermined period of time, such as when the sensor band is removed, the memory card or smart card is removed and inserted into a monitoring device which reads the stored health parameter data of the subject. The monitoring device includes a base station that includes a memory/smart card reader and is connected to conventional phone lines for transferring the collected data to a remote monitoring station. The base station may also capture additional clinical data, such as blood pressure data, and to perform data checks. Subject safety is enhanced by the ability of the base station to compare clinical data, e.g. ECG, against given profiles and to mark events when appropriate or when the base station is programmed to do so. The remote monitoring station allows the presentation and review of data (including events) forwarded by the sensor band. ECG analysis software and a user-friendly graphical user interface are provided to remotely analyze the transmitted data and to permit system maintenance and upkeep. In alternative embodiments, a smart card includes the sensor band's electronics and/or signal transmission circuitry in conjunction with a portable data logger so that the electronics may be reused from one disposable sensor band to the next without limiting the patient's range of movement. The system of the invention has useful application to the collection of subject clinical data during drug trials and medical testing for regulatory approvals as well as management of subjects with chronic diseases.

78 Claims, 21 Drawing Sheets

U.S. PATENT DOCUMENTS

| | | | |
|---|---|---|---|
| 3,212,496 A | 10/1965 | Preston | 128/2.06 |
| 3,409,007 A | 11/1968 | Fuller | 128/2.06 |
| 3,572,316 A | 3/1971 | Vogelman et al. | 128/2.05 |
| 3,572,322 A | 3/1971 | Wade | 128/2.06 |
| 3,603,881 A | 9/1971 | Thornton | 325/30 |
| 3,757,778 A | 9/1973 | Graham | 128/2.06 R |
| 3,848,582 A | 11/1974 | Milani et al. | 128/2.06 R |
| 3,858,576 A | 1/1975 | Dehnert et al. | 128/2.06 R |
| 3,882,277 A | 5/1975 | DePedro et al. | 179/2 DP |
| 3,902,478 A | 9/1975 | Konopasek et al. | 128/2.06 F |
| 3,908,641 A | 9/1975 | Judson et al. | 128/2.06 G |
| 3,943,918 A | 3/1976 | Lewis | 128/2.1 A |
| 3,986,498 A | 10/1976 | Lewis | 128/2.06 R |
| 4,023,564 A | 5/1977 | Valiquette et al. | 128/2.06 A |
| 4,082,087 A | 4/1978 | Howson | 128/2.06 E |
| 4,121,573 A | 10/1978 | Crovella et al. | 128/2.1 A |
| 4,121,575 A | 10/1978 | Mills et al. | 128/2.06 E |
| 4,122,843 A | 10/1978 | Zdrojkowski | 128/2.06 E |
| 4,141,351 A | 2/1979 | James et al. | 128/2.06 R |
| 4,202,344 A | 5/1980 | Mills et al. | 128/644 |
| 4,233,987 A | 11/1980 | Feingold | 128/639 |
| 4,249,538 A | 2/1981 | Musha et al. | 128/630 |
| 4,319,241 A | 3/1982 | Mount | 128/870.38 |
| 4,328,814 A | 5/1982 | Arkans | 128/640 |
| 4,353,372 A | 10/1982 | Ayer | 128/640 |
| 4,356,486 A | 10/1982 | Mount | 340/870.38 |
| 4,494,553 A | 1/1985 | Sciarra et al. | 128/721 |
| 4,522,211 A | 6/1985 | Bare et al. | 128/640 |
| 4,593,284 A | 6/1986 | Clifford et al. | 340/870.18 |
| 4,606,352 A | 8/1986 | Geddes et al. | 128/702 |
| 4,622,979 A | 11/1986 | Katchis et al. | 128/702 |
| 4,658,831 A | 4/1987 | Reinhard et al. | 128/697 |
| 4,662,378 A | 5/1987 | Thomis | 128/644 |
| 4,709,704 A | 12/1987 | Lukasiewicz | 128/644 |
| 4,742,831 A | 5/1988 | Silvian | 128/710 |
| 4,763,660 A | 8/1988 | Kroll et al. | 128/640 |
| 4,784,162 A | 11/1988 | Ricks et al. | 128/903 |
| 4,827,943 A | 5/1989 | Bornn et al. | 128/668 |
| 4,852,572 A | 8/1989 | Nakahashi et al. | 128/640 |
| 4,893,632 A | 1/1990 | Armington | 128/696 |
| 4,909,260 A | 3/1990 | Salem et al. | 128/721 |
| 4,926,868 A | 5/1990 | Larsen | 128/653 R |
| 4,955,381 A | 9/1990 | Way et al. | 128/640 |
| 4,957,109 A | 9/1990 | Groeger et al. | 128/640 |
| 4,967,748 A | 11/1990 | Cohen | 128/419 D |
| 4,967,749 A | 11/1990 | Cohen | 128/419 PG |
| 4,974,607 A | 12/1990 | Miwa | 128/904 |
| 4,981,141 A | 1/1991 | Segalowitz | 128/696 |
| 4,984,572 A | 1/1991 | Cohen | 128/419 D |
| 4,986,270 A | 1/1991 | Cohen | 128/419 D |
| 5,027,816 A | 7/1991 | Cohen | 128/419 PG |
| 5,038,782 A | 8/1991 | Gevins et al. | 128/644 |
| 5,050,612 A | 9/1991 | Matsumura | 128/670 |
| 5,069,215 A | 12/1991 | Jadvar et al. | 128/642 |
| 5,078,134 A | 1/1992 | Heilman et al. | 128/421 |
| 5,080,099 A | 1/1992 | Way et al. | 128/640 |
| 5,163,429 A | 11/1992 | Cohen | 128/419 PG |
| 5,168,874 A | 12/1992 | Segalowitz | 128/639 |
| 5,199,433 A | 4/1993 | Metzger et al. | 128/642 |
| 5,214,939 A | 6/1993 | Drucker et al. | 62/527 |
| 5,224,485 A | 7/1993 | Powers et al. | 128/696 |
| 5,228,449 A | 7/1993 | Christ et al. | 128/691 |
| 5,269,301 A | 12/1993 | Cohen | 607/6 |
| 5,279,305 A | 1/1994 | Zimmerman et al. | 128/731 |
| 5,307,817 A | 5/1994 | Guggenbuhl et al. | 128/696 |
| 5,307,818 A | 5/1994 | Segalowitz | 128/696 |
| 5,343,860 A | 9/1994 | Metzger et al. | 128/642 |
| 5,348,008 A | 9/1994 | Bornn et al. | 128/642 |
| 5,353,793 A | 10/1994 | Bornn | 128/642 |
| 5,372,125 A | 12/1994 | Lyons | 128/64 D |
| 5,373,852 A | 12/1994 | Harrison et al. | 128/733 |
| 5,394,882 A | 3/1995 | Mawhinney | 128/721 |
| 5,431,171 A | 7/1995 | Harrison et al. | 128/698 |
| 5,456,682 A | 10/1995 | Edwards et al. | 606/31 |
| 5,458,124 A | 10/1995 | Stanko et al. | 128/696 |
| 5,462,051 A | 10/1995 | Oka et al. | 128/630 |
| 5,465,715 A | 11/1995 | Lyons | 128/640 |
| 5,511,553 A | 4/1996 | Segalowitz | 128/696 |
| 5,522,396 A | 6/1996 | Langer et al. | 128/696 |
| 5,538,005 A | 7/1996 | Harrison et al. | 128/698 |
| 5,544,661 A | 8/1996 | Davis et al. | 128/700 |
| 5,549,113 A | 8/1996 | Halleck et al. | 128/671 |
| 5,558,638 A | 9/1996 | Evers et al. | 604/66 |
| 5,564,429 A | 10/1996 | Bornn et al. | 128/696 |
| 5,579,001 A | 11/1996 | Dempsey et al. | 340/870.01 |
| 5,579,775 A | 12/1996 | Dempsey et al. | 128/670 |
| 5,617,871 A | 4/1997 | Burrows | 128/696 |
| 5,634,468 A | 6/1997 | Platt et al. | 128/696 |
| 5,652,570 A | 7/1997 | Lepkofker | 340/573 |
| 5,670,944 A | 9/1997 | Myllymäki | 340/573 |
| 5,678,545 A | 10/1997 | Stratbucker | 128/640 |
| 5,682,902 A | 11/1997 | Herleikson | 128/708 |
| 5,687,717 A * | 11/1997 | Halpern et al. | 128/903 |
| 5,687,734 A | 11/1997 | Dempsey et al. | 128/696 |
| 5,701,894 A * | 12/1997 | Cherry et al. | 128/904 |
| 5,852,290 A * | 12/1998 | Chaney | 235/380 |
| 5,891,044 A | 4/1999 | Golosarsky et al. | 600/509 |
| 5,919,141 A | 7/1999 | Money et al. | 600/513 |
| 6,014,432 A | 1/2000 | Modney | 379/106.02 |
| 6,089,459 A * | 7/2000 | Eisele et al. | 235/441 |
| 6,093,146 A * | 7/2000 | Filangeri | 128/904 |
| 6,148,233 A * | 11/2000 | Owen et al. | 607/5 |
| 6,150,921 A * | 11/2000 | Werb et al. | 340/10.1 |
| 6,198,394 B1 * | 5/2001 | Jacobsen et al. | 600/301 |
| 6,275,681 B1 * | 8/2001 | Vega et al. | 455/343 |
| 6,324,211 B1 * | 11/2001 | Ovard et al. | 375/130 |

FOREIGN PATENT DOCUMENTS

| | | |
|---|---|---|
| EP | 0 479 857 B1 | 12/1993 |
| EP | 0 617 914 A1 | 10/1994 |
| EP | 0 458 883 B1 | 11/1996 |
| EP | 0 760 244 A1 | 3/1997 |
| EP | 0 761 160 A1 | 3/1997 |
| EP | 0 770 349 A1 | 5/1997 |
| EP | 0 719 108 B1 | 6/1997 |
| EP | 0 796 589 A1 | 9/1997 |
| EP | 0 796 590 A1 | 9/1997 |
| EP | 0 598 016 B1 | 10/1997 |
| EP | 0 959 607 A2 | 11/1999 |
| FR | 2 679 675 | 1/1993 |
| GB | 2 003 276 A | 3/1979 |
| GB | 2 207 579 A | 2/1989 |
| WO | WO 87/06447 | 11/1987 |
| WO | WO 90/01898 | 3/1990 |
| WO | WO 91/00054 | 1/1991 |
| WO | WO 93/02622 | 2/1993 |
| WO | WO 93/08734 | 5/1993 |
| WO | WO 93/10706 | 6/1993 |
| WO | WO 93/19667 | 10/1993 |
| WO | WO 94/01039 | 1/1994 |
| WO | WO 94/03105 | 2/1994 |
| WO | WO 94/25841 | 11/1994 |
| WO | WO 95/07048 | 3/1995 |
| WO | WO 95/07652 | 3/1995 |
| WO | WO 95/10974 | 4/1995 |
| WO | WO 96/01585 | 1/1996 |
| WO | WO 96/29005 | 9/1996 |
| WO | WO 96/38080 | 12/1996 |
| WO | WO 97/09923 | 3/1997 |
| WO | WO 97/28736 | 8/1997 |
| WO | WO 97/40747 | 11/1997 |

| WO | WO 00/62664 | 10/2000 |

OTHER PUBLICATIONS

"Biomedical Telectrodes: Compact transmitters would eliminate the need for wires to monitors," *Nasa TechBrief*, Lyndon B. Johnson Space Center, Houston, Texas, Feb. 1990, 1 page.

U.S. patent application Ser. No. 09/292,157, filed Apr. 15, 1999.

U.S. patent application Ser. No. 09/292,159, filed Apr. 15, 1999.

U.S. patent application Ser. No. 09/292,405, filed Apr. 15, 1999.

U.S. patent application Ser. No. 09/590,996, filed Jun. 9, 2000.

* cited by examiner

FIG. 11B

Monitoring Setup

Patient Number: 123
Group Study Code: 321

| Monitoring and Download Scheule | Event setup | Auxiliary Sensor Setup |

This page specifies the schedule of patient monitoring and the schedule for downloading data from the Base Station

Monitoring days
- ⦿ Monitor every day
- ○ Monitor only on these days ☑ Monday ☑ Tuesday ☑ Wednesday ☑ Thursday ☑ Friday ☑ Saturday ☑ Sunday

Monitoring times
- ⦿ Monitor at 14:00:00  19:00:00
- ○ Monitor every 1 hour(s) 00 minute(s) past the hour, starting at 00:00:00
- Monitor for 1 hour(s) and 00 minutes

Download days
- ⦿ Download every day
- ○ Download only on these days ☑ Monday ☑ Tuesday ☑ Wednesday ☑ Thursday ☑ Friday ☑ Saturday ☑ Sunday

Download time
Download data from patient at 00:00:00

[Save Changes] [Undo Changes]
[Print] [Close]

???? Sensor Changes Saved.    01/04/99  19:20

PORTABLE REMOTE PATIENT TELEMONITORING SYSTEM USING A MEMORY CARD OR SMART CARD

CROSS-REFERENCE TO RELATED APPLICATIONS

The present application is a continuation-in-part application of U.S. patent application Ser. No. 09/292,405, filed Apr. 15, 1999.

BACKGROUND OF THE INVENTION

1. Field of the Invention

The present invention relates to a system and method for monitoring vital signs and capturing data from a patient remotely using telemonitoring techniques. In particular, the present invention is a low cost, patient-friendly, ambulatory monitoring system incorporating a low cost memory card or smart card for the remote electronic capture of noninvasive vital signs data including, e.g., full single or multiple lead ECG, respiration rate, $SpO_2$, skin temperature, and blood pressure.

2. Description of the Prior Art

Before drugs and related therapies are approved for widespread use by physicians, such drugs and therapies typically undergo numerous trials for efficacy and safety. Successful human trials are critical to regulatory approval of a new drug or therapy, and accordingly, much money and effort goes into the human trials. At present, patients are selected for the trial and placed on the regimen under test. The efficacy and safety of the drug and/or therapy is tested by having the patient make numerous visits to his or her physician for testing during the trial period. While a great deal of information can be gathered at such tests, generally there is no method for collecting the data between physician visits, thereby causing decisions regarding efficacy and safety to be made base on a small sampling of the patients' experiences with the drug and/or therapy. More frequent visits to the physician would improve the data pool; unfortunately, such visits are expensive, add to the overall cost of the trial, and, because a limited data set is available, the trial duration is lengthened, thereby delaying the drug's market introduction.

An improved technique for testing the efficacy and safety of a drug and/or therapy is desired which does not require additional visits to the physician. It is desired to develop a technique for collecting data from a human subject at all times during a trial without requiring any visits to the physician's office, thereby eliminating the cost and inconvenience of visiting the physician's office for routine monitoring.

Also, an improved remote patient monitoring/management system is generally desired whereby useful vital signs data may be obtained from a patient without requiring frequent visits to the physician's office. Such remote monitoring/management is particularly desirable for home patient monitoring of patients with chronic illnesses such as congestive heart failure or for post-operative or out-patient monitoring. Prior art patient telemetry systems have had limited commercial success for a variety of reasons such as difficulty of use and cost.

Remote patient monitoring techniques are generally known in which electrodes are placed on the patient to monitor the patient's vital signs and the captured data is transmitted to a remote display for monitoring the patient's condition. Remote monitoring systems are known which permit a doctor or nurse to monitor the conditions of several hospitalized patients from a central monitoring site in the hospital. Typically, sophisticated patient monitoring equipment is used to collect data from the patient, and the collected data is transmitted via wire to the central monitoring site in the hospital. Generally, wireless systems are problematic in the hospital setting because of the proximity of the respective patients and the amount of interference found in such a setting.

Most of the patients receiving a particular drug regimen or therapy being tested are ambulatory and, in many cases, participating in the study from home. Remote monitoring of patients from their homes introduces an entirely new set of challenges for transmitting the gathered data to a central location for evaluation. Numerous attempts have been made to facilitate such data collection and transmission; however, in each case, cumbersome and uncomfortable monitoring equipment is placed on the patient and the patient is tethered to the monitoring equipment by electrical cords, thereby limiting the patient's movement. In some prior art systems, the electrical cords have been removed and the transmissions to the monitoring equipment made using telemetry techniques; however, such systems have been used primarily for real-time vital signs monitoring and not for data collection of the type needed for diagnosis and efficacy and safety testing. Moreover, such systems also limited the movement of the patient to a limited area near the vital signs monitor.

For example, an early telemetry system is described in U.S. Pat. No. 3,603,881 in which short transmission distances to a building's wiring system are covered using VHF transmission. Physiologic data such as electrocardiographic (ECG) data is collected by a sensor and transmitted by a VHF transmitter to a fixed VHF receiver RF transmitter coupled to the wiring system in the building. A RF receiver demodulator monitor is coupled to the building's wiring system at the nurse's station for receiving the physiologic data for patient monitoring and/or data recording.

A similar telemetry system for monitoring ECG signals is described in U.K. Patent Application No. 2 003 276 except that telephone connections are used in place of the building wiring and the system is also designed to collect blood pressure, pulse rate, respiratory rate and the like and to relate that information to the physician via the telephone connections.

Other early telemetry systems of the type described by Lewis in U.S. Pat. No. 3,943,918 and by Crovella et al. in U.S. Pat. No. 4,121,573 use telemetric techniques to transmit data from a sensor device attached to the patient's chest via RF to a radio telemetry receiver for display and/or recording as desired. S. S. Ng describe yet another telemetry system for ECG monitoring in an article entitled "Microprocessor-based Telemetry System for ECG Monitoring," IEEE/Ninth Annual Conference of the Engineering in Medicine and Biology Society, CH2513-0, pages 1492–93 (1987). Ng therein describes a system for providing continuous ECG monitoring and analysis by means of a PC AT via wireless link. In the Ng system, the patient requires a transmitter that is carried by the patient for sensing and transmitting the patient's ECG signal to a central base station via wireless link. At the base station, a receiver recovers the original ECG signal from a few patients simultaneously for display.

Each of the above-described telemetry systems is designed primarily for hospital use and include relatively expensive sensor arrays and processing devices for real-time patient monitoring and diagnosis. The real-time monitoring is generally used in an "alarm" mode to capture events, rather than to collect data over a period of time to determine trends which might indicate a more gradual deterioration or improvement in the patient's condition or to predict a forthcoming event. Also, these systems require the patient to remain in close proximity to the base stations including the receivers.

Bornn et al. describe a portable physiological data monitoring/alert system in U.S. Pat. Nos. 4,784,162; 4,827, 943; 5,214,939; 5,348,008; 5,353,793; and 5,564,429 in which a patient wears a sensor harness including a microprocessor that detects potentially life-threatening events and automatically calls a central base station via radiotelemetry using a radio modem link. In a home or alternate site configuration, communications between the base station and remote unit is by way of commercial telephone lines. Generally, the system automatically calls "911" or a similar emergency response service when an abnormality is detected by the ECG monitor. Unfortunately, the sensor harness is quite cumbersome and conspicuous and includes sensors for performing an alert function rather than data collection and analysis functions.

Segalowitz discloses a wireless vital signs monitoring system in U.S. Pat. Nos. 4,981,141; 5,168,874; 5,307,818; and 5,511,553 including aprecordial strip patch including a multi-layer flexible structure for telemetering data by radio frequency or single wire to hardware recording apparatus and a display monitor. Microsensors and conductive contact elements (CCEs) are mounted on the strip patch so as to permit simultaneous and continuous detection, processing and transmission of 12-lead ECG, cardiac output, respiration rate, peripheral blood oximetry, temperature of the patient, and ECG fetal heart monitoring via a single wavelength of radio frequency transmission. While the precordial strip patch used by Segalowitz purportedly transmits vital signs data up to 50 meters, it requires a dual-stage operational amplifier chip, an encoder modulator chip, a wireless transmitter chip including an oscillator, and other costly components such as artificial intelligence software, sound and visual alarms, and a microprocessor. As a result, the precordial strip patch is relatively expensive to manufacture and operate. Also, as with the other telemetry systems noted above, the emphasis of Segalowitz is on real-time monitoring and alerting of medical personnel to immediate medical needs of the patient.

Platt et al. also disclose a sensor patch for wireless physiological monitoring of patients in U.S. Pat. No. 5,634, 468. Platt et al. describe a sensor and system for monitoring ECG signals remotely from patients located in non-hospital sites. In this system, a sensor patch containing sensing electrodes, signal processing circuitry and radio or infra-red transmission circuitry is attached to the patient's body and preferably worn for at least a week before its power supply is exhausted and the sensor patch is thrown away. A receiver at a primary site in the vicinity of the patient receives the data transmitted by the sensor patch and stores the sensed data. When the patient feels discomfort or concern, or if the portable unit sounds an alarm, the patient telephones the monitoring station and downloads the stored data from the portable unit via the standard voice telecommunications network. The downloaded ECG data is then monitored and analyzed at the monitoring station. The receiver in the proximity of the patient may be a portable unit carried around by the patient, where the portable unit includes a receiver, a processor for processing the received data to identify abnormalities, a memory for storing the sensed data, and circuitry for interfacing to a telephone line to send the ECG data signals to the monitoring station. The monitoring station decodes the received ECG signals and performs beat and rhythm analysis for classification of the ECG data. If an abnormal condition is discovered, medical personnel in the vicinity of the patient are contacted. While the system described by Platt et al. may collect ECG data from the patient and process it at a remote monitoring station, the data is only collected when the patient initiates the data download. Otherwise, data is lost once the memory in the portable unit is full. No mechanism is provided for continuously collecting data, at all times, in a way which requires little or no patient action.

In U.S. Pat. No. 5,522,396, Langer et al. disclose a telemetry system for monitoring the heart of a patient in which a patient station includes telemetering apparatus for transmitting the outputs of patient electrodes to a tele-link unit connected to a monitoring station by telephone lines. As in the Platt et al. system, Langer et al. transmit ECG data to a central location. However, unlike the Platt et al. system, the Langer et al. system checks the ECG data for predetermined events and automatically calls the monitoring station when such events are detected. A similar telemetry system is described by Davis et al. in U.S. Pat. No. 5,544,661 which initiates a cellular phone link from the patient to the central monitoring location when an event is detected. As with the Platt et al. system, the Davis et al. system does not provide a mechanism for continuously collecting data with little or no patient action.

Accordingly, a telemonitoring system is desired which collects vital signs data from a patient using an inexpensive device that permits the continuous collection of a patient's vital signs data with little or no patient action. Also, a data management system is desired which permits the collected data to be reviewed and formatted for use in patient trials and the like. The present invention has been designed to meet these needs in the art.

SUMMARY OF THE INVENTION

The present invention meets the above-mentioned needs in the prior art by providing a portable remote patient telemonitoring system which collects vital signs (health parameter) data from a patient using a disposable sensor device attached to the patient and stores the vital signs data on a memory card or a smart card that may be inserted into the sensor device for data collection and/or transmits the data to a portable data logger or base station unit for processing and storage. In a first embodiment, a memory card is used that stores the vital signs data and is removed and its contents downloaded to a monitoring device for performing processing and monitoring functions. In a second embodiment, the electronics of the disposable sensor device are provided on a removable smart card-type device that may or may not have memory for storing the collected vital signs data. The electronics on the smart card may or may not include transmission circuitry for transmitting the vital signs data to a nearby portable data logger or a base station unit. Each embodiment of the portable remote telemonitoring system in accordance with the invention is characterized by combinations of the following separate elements, each with different functions within the system.

The first component is an adhesive, cordless, disposable sensor band with electrode patches, other sensors, and a connector dock for accepting a conventional memory card, such as an MMC memory card, for storing detected vital signs data, or a smart card that contains electronic circuitry and may or may not contain memory. Additional internal memory equivalent or discrete memory may also be available on the memory card or smart card. The smart card preferably includes the sensor band's electronics so that the cost of the disposable sensor band may be minimized. The sensor band is easy-to-use and is positioned on the patient by the patient. The sensor band is designed to be worn comfortably by the patient for 24 hours, at which time the sensor band may be discarded and replaced by a new sensor band. The memory card or smart card is ideally designed to store all vital signs data generated by the patient during that 24 hour period. The memory card or smart card is removed from the sensor band before the sensor band is discarded, and the memory card or smart card is either mailed or carried to a remote monitoring station or, more preferably, inserted into a base station which uploads the stored vital signs data to the remote monitoring station. Since the vital signs data is collected on a memory card or smart card received in the sensor band, the patient is free to move around freely while his or her vital signs are being monitored. Once the data stored on the memory card or smart card is uploaded, the memory card or smart card may be used again with another sensor band.

The second component is a base station having a memory card/smart card reader for accepting the memory card or smart card, reading the vital signs data stored therein, and storing the vital signs data until the stored data is to be uploaded via conventional phone lines to a remote monitoring station. The base station may also be designed to capture additional clinical data, such as blood pressure data, to perform data checks, and to process the stored data. For data transfer, the base station connects the memory card or smart card, via modem and land or cellular telephone line, to the remote monitoring station. Connections for auxiliary sensors such as a blood pressure cuff extend the number of clinical parameters that can be captured. Patient safety is enhanced by the ability of the base station to compare clinical data, e.g. ECG, against given profiles and to indicate violation of preset limits when appropriate or when the base station is programmed to do so. Such violations could be indicated to the patient by audio and/or visual indicators.

The third component is a remote monitoring station that allows the presentation and review of data (including event flags) forwarded by the sensor band and other sensors and simply requires a standard PC running, e.g., Windows NT. ECG analysis software and a user-friendly graphical user interface are provided to remotely analyze the transmitted data and to permit system maintenance and upkeep.

In a preferred embodiment, the patient health parameter data collection and monitoring system of the invention is characterized by a sensor band having a sensor assembly for application to a subject, where the sensor assembly produces health parameter data indicative of values of at least one health parameter of the subject. The sensor band in accordance with the invention includes a connector that accepts a memory card, such as a low cost MMC memory card, that includes internal memory for storing the health parameter data produced by the sensor band, or a specially designed smart card that contains the signal processing circuitry (ADC, etc.) as well as any desired memory. The memory card or smart card is then removed and inserted into a monitoring station including a memory card/smart card reader which is adapted to read the health parameter data from the memory card or smart card for display or further processing. The memory card or smart card may be taken or mailed to a remote monitoring station for data download, or, conversely, the memory card or smart card may be inserted into a base station at the patient's location for uploading the health parameter data from the memory card or the smart card to the remote monitoring station via a telecommunications link. The remote monitoring station captures the vital signs data and stores it in a database for display and subsequent access. The remote monitoring station also processes the health parameter data for medical diagnosis or analysis. In the preferred embodiment, the remote monitoring station stores the health parameter data in the database with the vital signs data from a plurality of other patients. A user interface provides access to the vital signs data in the database for processing, medical diagnosis and/or analysis.

As noted above, the smart card also houses the sensor band's electronics so that the electronics may be reusable from one sensor band to the next. Such electronics may include a rechargeable power supply that is recharged when the memory card or smart card is inserted into the base station unit for data download. Alternatively, the power supply may reside on the sensor band (e.g., in the smart card/memory card connector) and be discarded with the disposable sensor band when the power supply is depleted.

In presently preferred embodiments, the sensor band measures full waveform single or multiple lead ECG, full waveform respiration, skin temperature, and motion and stores the measured data in the memory card or smart card. Auxiliary sensors are preferably provided at the base station, such auxiliary sensors including, e.g., a blood pressure cuff, a spirometer, and weight scales. Also, the user interface at the remote monitoring station may contain full ECG analysis software covering waveform measurements, interval measurements, beat-typing and arrhythmia detection. "Event flags" also may be generated and indicated to the physician for high and low heart rate, high and low respiration rate, high and low temperature, high and low blood pressure or arrhythmias.

While there are many potential patient management applications for the remote telemonitoring system of the invention, such as remote measurement of cardiovascular abnormalities including hypertension, congestive heart failure, arrhythmia, silent ischaemia, and the like, and respiratory abnormalities including chronic obstructive pulmonary disease, in a presently preferred implementation of the invention, the remote telemonitoring system of the invention is also designed to reduce both the length and the cost of clinical drug trials by providing versatility in data collection with respect to site (in-clinic or domiciliary), time, and volume, and to provide direct, electronic data capture. Additional applications include the monitoring of sleep apnea, diabetes, acute or sub-acute infection, asthma, and the like, as well as "remote nurse" applications which provide a live view of the patient's condition. However, those skilled in the art will appreciate that the use of a memory card or such a smart card is not well-suited to real-time vital signs monitoring unless the smart card includes transmission circuitry. Such transmission circuitry is included in another embodiment of the invention whereby the smart card includes transmission circuitry for broadcasting the vital signs data to a portable data logger or base station unit for remote storage. In such an embodiment, the smart card may or may not contain memory for storing the vital signs data and may or may not include the sensor electronics. However, the inclusion of some memory on the smart card is preferred as it may act as a buffer in the event that the transmission channel with the portable data logger or base station unit is lost for some reason (e.g., the sensor band is out of range).

Though generally applicable to patient home use, those skilled in the art will appreciate that the system of the invention also may be used in a clinic or hospital setting. Corresponding methods of collecting a patient's vital signs data using the remote telemonitoring system of the invention are also described and claimed herein.

BRIEF DESCRIPTION OF THE DRAWINGS

The above and other objects and advantages of the invention will become more apparent and more readily appreciated from the following detailed description of a presently preferred exemplary embodiment of the invention taken in conjunction with the accompanying drawings of which:

FIG. 11B illustrates the case home screen listing the events which occurred for the selected patient during the selected time interval.

FIG. 11C illustrates the monitoring setup change screen available for the selected patient.

FIG. 11D illustrates the patient information listing the patient data for the selected patient.

FIG. 11E illustrates the auxiliary sensors setup screen available for the selected patient.

DETAILED DESCRIPTION OF PRESENTLY PREFERRED EMBODIMENTS

A system and method with the above-mentioned beneficial features in accordance with a presently preferred exemplary embodiment of the invention will be described below with reference to FIGS. 1–12. It will be appreciated by those of ordinary skill in the art that the description given herein with respect to those figures is for exemplary purposes only and is not intended in any way to limit the scope of the invention. All questions regarding the scope of the invention may be resolved by referring to the appended claims.

I. System Overview

Figure 1:
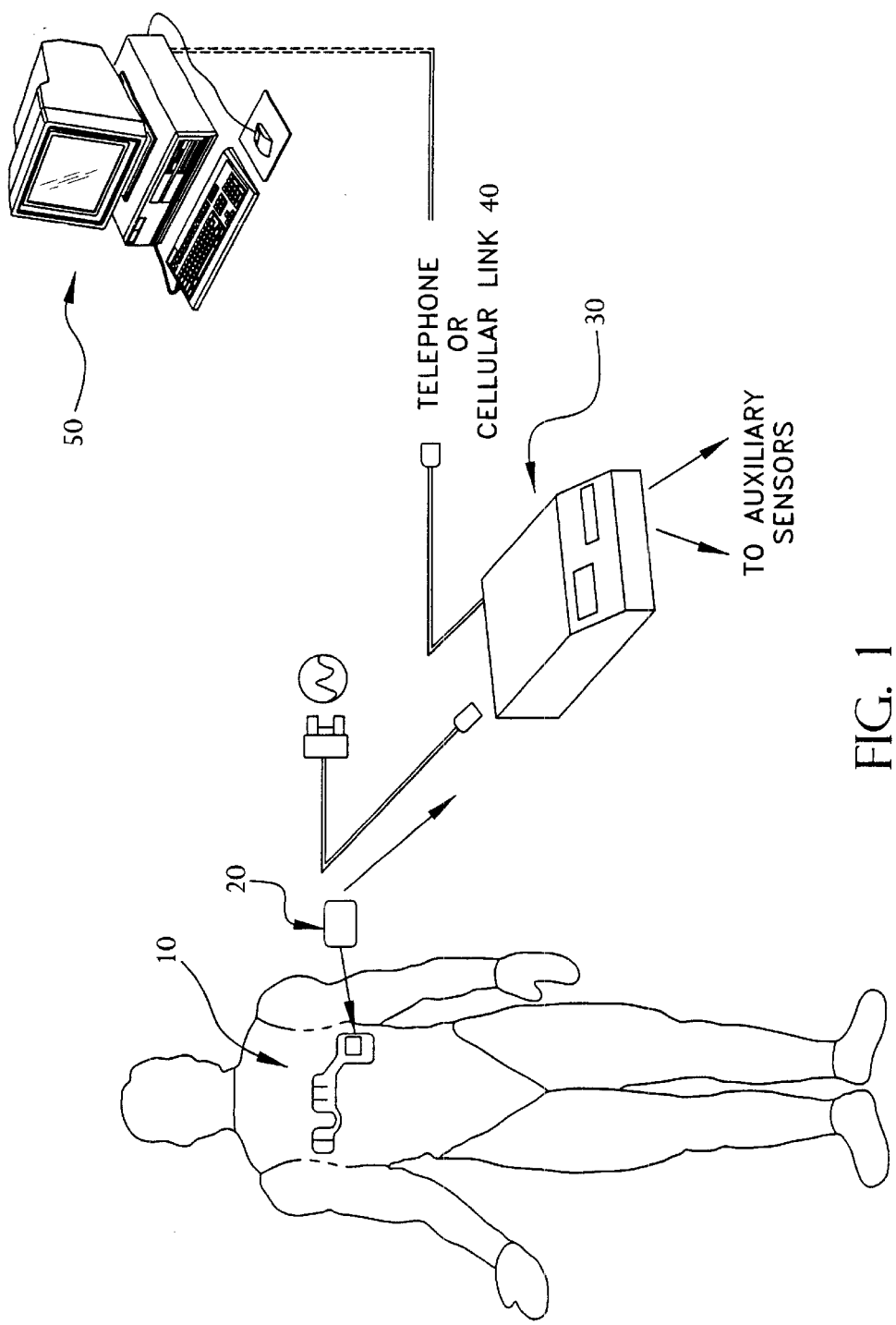
FIG. 1 illustrates a presently preferred embodiment of the remote patient monitoring system in accordance with the invention.

A presently preferred embodiment of the remote patient telemonitoring system of the invention is illustrated in FIG. 1. As illustrated, the system of the invention comprises a disposable multi-parameter sensor band 10, preferably worn on the patient's chest, for measuring patient vital signs (health parameters) and storing the measured vital signs data in a memory card/smart card 20 and/or transmitting the measured vital signs data to a portable data logger (not shown) carried by the patient, a base station unit 30 which receives the stored vital signs data from the memory card/smart card 20 and transmits the vital signs data over a telecommunications link 40, and a remote monitoring station 50 which receives the vital signs data from the base station unit 30 via the telecommunications link 40. The operation of each of the components of the system will be described in more detail below.

A. Multi-Parameter Sensor Band

Figure 2:
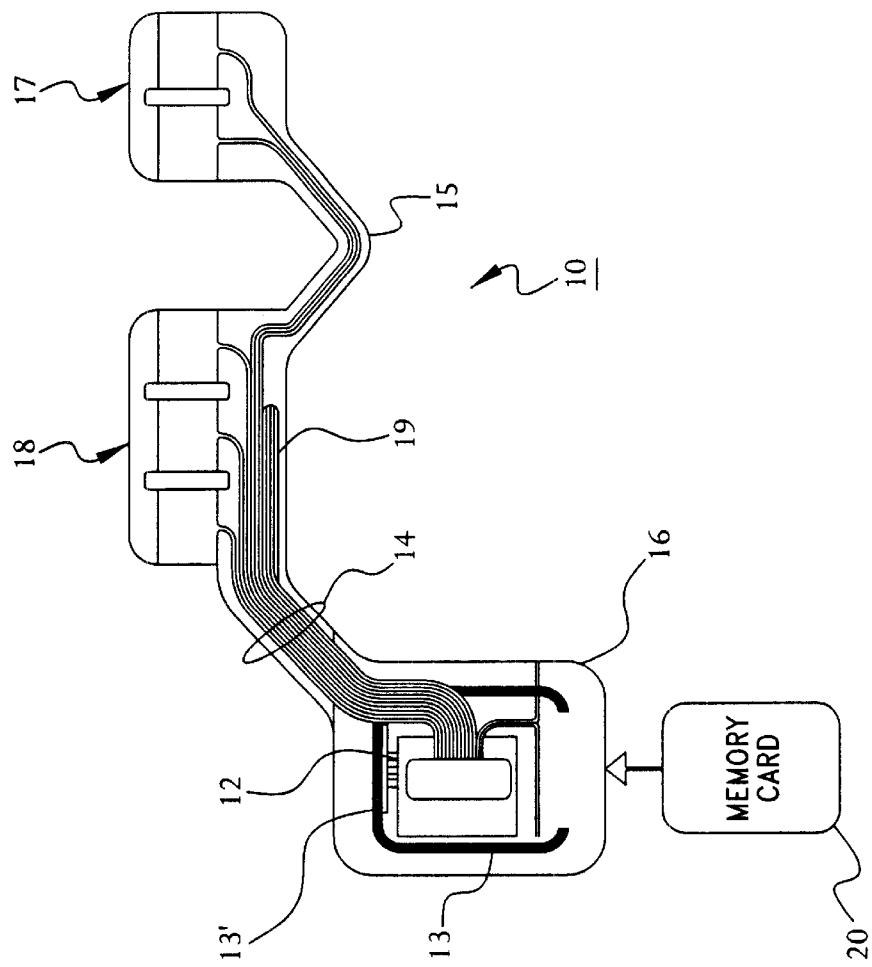
FIG. 2 illustrates a rear view (patient side) of a sensor band including electrodes and sensors for attachment to the patient's body for measuring vital signs data such as full waveform single or multiple lead ECG, full waveform chest respiration, $SpO_2$, skin temperature, and motion using the techniques of the invention.

As illustrated in FIG. 2, the sensor band 10 is designed to extend across the patient's chest and includes electrodes and other sensors (not shown) which are situated so as to measure full waveform single or multiple lead ECG, full waveform chest respiration (using impedance and/or resistance bend sensor), skin temperature, and motion. Of course, other vital signs, such as EEG and blood oxygenation, could be measured as desired using sensors included within the existing sensor band and placed either on the chest or elsewhere on the body, or using sensors in another sensor band placed either on the chest or elsewhere on the patient's body. Conventional blood oxygenation sensors placed on the finger, wrist, or ear may also provide data through a wire or wireless link to the sensor band 10. The signal processing circuitry 12 receives the sensor data from traces 14 and a directly connected thermistor (not shown) and is powered by, e.g., an alkaline manganese battery pack (not shown) designed to permit the sensor band 10 to collect vital signs data for approximately 30 hours and to store the collected vital signs data in a memory card/smart card 20 connected to the signal processing circuitry 12 through a connector 13' of the connector port 13 disposed atop the signal processing circuitry 12 so as to accept the memory card/smart card 20. As explained in more detail below, the smart card differs from the memory card in that it also includes the signal processing circuitry 12 whereby all the sensor band's electronics are on the smart card 20. In this case, the smart card 20 is connected to a connector that is, in turn, connected directly to the traces 14. As also explained below, the batteries for powering the smart card may be housed in the connector and discarded with the used sensor band 10, or, alternatively, the smart card 20 may include rechargeable battery elements.

The sensor band 10 is typically removed and disposed of every 24 hours and replaced by a new sensor band 10. Upon power up of the new sensor band 10, the serial number of that sensor band 10 is randomly generated and sent in a repeating cycle for easy tracking of the vital signs data stored in the memory card/smart card 20. The sensor band 10 is designed such that the patient only has to prepare his or her skin, peel back a protective strip over the hydrogel and hydrocolloid adhesive layers which are, in turn, placed over the electrodes, signal processing circuitry 12, and battery, and stick the sensor band 10 to the prepared skin in a position for measurement of the vital signs such as ECG. If a memory card or smart card 20 rather than internal memory is used, the patient then inserts the memory card/smart card 20 into the connector port 13 until it engages the connector 13'. The sensor band 10 may be provided in a number of sizes sufficient to administer to infants as well as large adults. The "V" bend 15 is preferably located between the left and right chest sections so as to allow some movement of the sensor band 10 when it is attached to the chest.

In a presently preferred embodiment, full waveform ECG data is collected at a 250 Hz sampling frequency from three electrodes: one electrode in portion 16 placed under the patient's left armpit, one electrode in a portion 17 on the right hand side of the chest, and one reference electrode in portion 18 on the left hand side of the chest. The ECG data is collected with a resolution of 10 bits.

Full waveform respiration data is also collected at a 25 Hz sampling frequency using the trans-thoracic impedance method, with a 50 kHz continuous reciprocating current and two electrodes (force and sense) at the left hand side of the chest and two electrodes at the right hand side of the chest. The sense electrode on the right hand side of the chest is preferably the same as that used for ECG detection. The respiration data has a data resolution of 8 bits. Respiration data (with the same qualities except for 7 bit resolution) may also be collected using a printed carbon on flextrate resistance bend sensor 19 located on the left hand side of the chest. One or both methods of respiration measurement may be used for a given patient.

Skin temperature data is collected at 25 Hz using a thermistor located in portion 16 under the armpit. The temperature range is 25 to 45 degrees C. with a reporting accuracy of +/−0.5 degree C., an output sampling frequency of 25 Hz, and data resolution of 6 bits.

Motion data is collected at 25 Hz sampling frequency using impedance sensing across the chest using the same drive electrodes as those described for respiration above. The motion data has a data resolution of 6 bits. In a preferred embodiment, the motion data may be compared to the ECG waveform and/or respiration waveform to determine if the measured data has been corrupted by movement.

In modified embodiments, additional data, such as blood oxygen saturation data either from a finger or ear band or included within the chest sensor band 10, may also be collected and provided to the sensor band 10 via a wired or wireless connection for storage on memory card/smart card 20.

Signal processing circuitry 12 preferably includes a microcontroller, such as an Atmel Atmega 103 microcontroller, to take and collect physiological measurements and to amplify, filter, and signal process the analog data from the sensors, perform analog to digital data conversion at 10 bit accuracy using an on-chip ADC (with subsequent reduction for all but the ECG signal), and then format the data stream into a predetermined format for storage in memory/smart card 20 or for transmission by a PIC microcontroller (not shown) to a transmitter of the smart card 20 at an appropriate data bit rate. During normal operation, digital data is obtained from five channels of the ADC and the UART. A 10 bit ECG measurement is made of each of the leads of the ADC (corresponding to each of the ECG leads) every 4 msec. Preferably, a respiratory measurement and a battery voltage measurement are also made via the ADC every 4 msec., also at 10 bit resolution. However, only one reading of each of these parameters is needed every 40 msec; the remaining readings may be discarded. An external oximeter may provide a three byte measurement via the UART every second, only one byte of which is needed. In normal operation, the rate of data collection is therefore: 3×10×250=7500 bits/second ECG data; 2×10×25=500 bits/second for respiration and battery voltage data; and 1×8×1=8 bits/second oximetry data, for a total of 8008 bits/second.

As will be noted below with respect to FIGS. 5A–5D, the functionality of the microcontroller(s) will vary depending upon whether the smart card is equipped only for data storage (and hence is a memory card) or is also equipped for data transmission. The micro-controller(s) of the signal processing circuitry 12 are mounted on a flexible or rigid PCB of the sensor band 10, which also contains passive components (resistors, capacitors etc.), a crystal, batteries, and connections. The PCB is connected to a flexible substrate which has printed circuit traces 14 providing connections to the electrodes and the connector 13'. More details concerning the design and manufacture of the sensor band 10 can be found in U.S. patent application Ser. Nos. 09/292,159 and 09/292,157 also assigned to the present assignee.

Alternatively, as explained in more detail below with respect to FIG. 5, the signal processing circuitry 12 may be included in the smart card 20 so that the signal processing circuitry 12 may be reused from one sensor band 10 to the next. The signal processing circuitry 12 may also receive SpO2 measurements from an external oximeter via the UART of the ATmega 103 and arrange the measurements into a predetermined format for transmission to a personal data logger 22 (described below). The signal processing circuitry 12, whether on the sensor band 10 or on the smart card 20, also may monitor the status of its circuitry and/or the battery level and indicate in a transmitted message if there is a hardware fault or a low battery level. It should be noted that the ATmega 103 contains 4 k of RAM for use as a stack, data buffers, and variable storage and 128 k of programmable flash memory for program and constant storage. The ATmega 103 also contains 4 k of EEPROM to store configurable parameters used by any software implemented by the processing circuitry of the smart card 20.

As used herein, a "memory" card differs from a "smart" card in that a memory card includes memory only, while a smart card also includes signal processing circuitry, such as an A/D converter and transmission circuitry and/or a rechargeable battery.

Those skilled in the art will appreciate that for the memory/smart card 20 to be able to store vital signs data for up to 30 hours it must be large enough to store up to several gigabytes using the sampling rates described herein and no data compression. In a currently preferred embodiment, data compression is used with a memory/smart card capable of holding at least 96 MB of compressed data so that selected data may be captured over a 24 hour period. Of course, larger or smaller memory devices may be used as desired in accordance with cost and availability and the availability of sufficient processing power for data compression.

B. Base Station Unit

Base station unit 30 is powered by a selectable 110/230V mains power supply and includes a modem connection for a land telephone line or cellular link 40. The modem is used to send data to a remote monitoring station 50 at a remote telemonitoring center, which may be a physician's office or a hospital. In using the base station unit 30, the patient will need to ensure that it is switched on and that the telephone line 40 is connected. Otherwise, the base station unit 30 operates automatically, with no further action required by the patient, other than the use of auxiliary sensors.

In a first embodiment, a base station unit 30 can only receive vital signs data from a memory/smart card 20. Of course, memory/smart cards from a plurality of patients may be inserted into the base station unit 30 to be read, and the vital signs data from each memory/smart card 20 may be separately stored based on patient identification information stored on the memory/smart card 20 with the vital signs data. Hence, a single base station unit 30 may service a facility such as a hospital.

Figure 3:
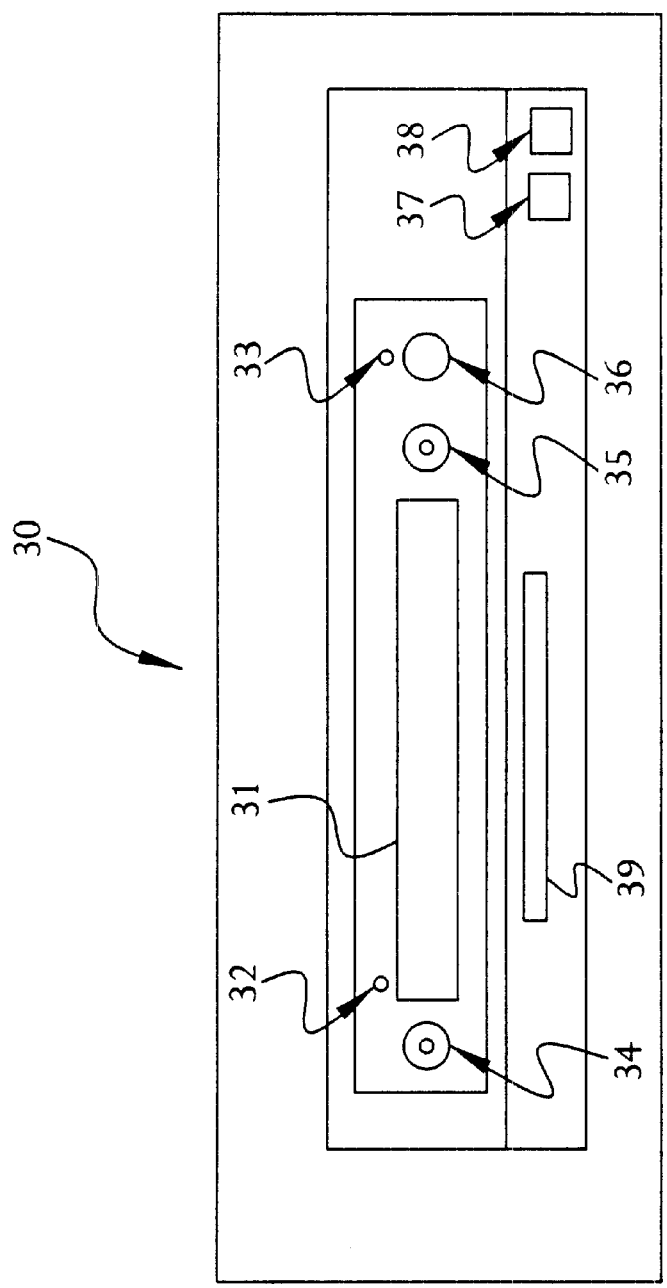
FIG. 3 illustrates the user interface to the base station unit provided in accordance with the invention.

As illustrated in FIG. 3, the base station unit 30 may include a liquid crystal display screen 31 which provides information regarding system operation and gives the patient guidance when stepping through the options for collecting data from an auxiliary sensor. A light 32 indicates that the base station unit 30 is receiving mains power. A similar light 33 may be used to indicate that the base station unit 30 is communicating with the remote monitoring station 50 via modem. An auxiliary sensor button 34 illuminates to indicate that an auxiliary sensor measurement is due, and the auxiliary sensor button 34 may be pushed to acknowledge when an auxiliary sensor measurement is about to be started and when it has been completed. A buzzer silence button 35 is preferably provided to silence the buzzer (not shown), which will sound to indicate that a message is to be read on the display screen 31. A telephone hang-up button 36 preferably breaks the communication between the base station unit 30 and the remote monitoring station 50 when depressed so that normal use of a phone connected to the same telephone line either directly or via a base station port is enabled, e.g., in emergency situations.

As noted above, the base station unit 30 preferably includes the facility for the connection of a blood pressure sensor to a connector 37 or a spirometer or weigh scales to a connector 38. The blood pressure sensor and spirometer are preferably standard commercially available units with standard RS232 digital data output streams. The base station unit 30 has electrical isolation to these units. Alternatively, other point in time sensors such as a blood glucose meter could be connected to either connector 37 or 38. A memory/smart card reader 39 accepts memory/smart card 20 for reading the vital signs data stored thereon and, if rechargeable battery power is included on the memory/smart card 20, for recharging the battery power.

During operation, the base station unit 30 reads a memory/smart card 20 or its equivalent inserted into the memory/smart card reader 39 and stores all data received therefrom in an internal memory. Preferably, the internal memory of the base station unit 30 is a hard disk memory, enabling storage of data until it is ready to be sent to the remote monitoring station 50. In a presently preferred embodiment, a memory having the capability of storing several days (e.g., 7 days) of data (at least 2 GB of memory at the sample rates described herein and assuming no data compression) is desired. Preferably, the sensor data from the sensor band 10, any event data (threshold violations and the like described below), and the auxiliary measurement data (spirometer, weight scales, and/or blood pressure) are stored separately and aged independently in the memory of the base station unit 30 based on time stamps from the sensor band 10 that may be stored on the memory/smart card 20 to enable synchronization of the time stamps of the sensor band 10 and the base station unit 30. All data is retained in the base station memory until either it is directed to be discarded by an instruction sent from the remote monitoring station 50, or until the base station memory is full, at which point the earliest data is discarded first.

In the preferred embodiment, the base station unit further contains software algorithms which enable the calculation of heart rate and respiration rate from the ECG and respiration signals, respectively. Such algorithms include artefact detection and filtering to ensure that a high quality reading is obtained. Preferably, the algorithm for heart rate also includes a 50 Hz/60 Hz notch filter for removal of any mains noise. The base station may further contain a look-up table to convert signals received from the thermistor of the sensor band 10 into an accurate temperature reading. Preferably, the base station unit 30 creates a summary of the collected data for transmission so as to minimize the duration of the transmission time to the remote monitoring station 50. The contents of the summary may be specified in requests from the remote monitoring station 50.

The base station unit 30 may also include software which compares the various vital signs data signals received with pre-programmed thresholds for certain physiological variables. In particular, the base station unit 30 may look for threshold violations; however, the actual processing for determining whether an "event" has occurred is performed when processing the raw data at the remote monitoring station 50. Where data points fall outside these threshold values for a certain period of time, the base station unit 30 may record an event condition. Events are preferably generated for high or low heart rate, high or low respiration rate, or high or low temperature. The inventors also contemplate that, in alternative embodiments, events could be generated for high or low blood pressure, ischaemic events, or arrhythmias. When an event is generated, the buzzer on the base station unit 30 may be sounded and the buzzer silence button 35 may be illuminated. A warning message could also be displayed on display 31. The buzzer and/or warning message would warn the patient to call his/her doctor to investigate an event which occurred that day, presumably without the patient's knowledge. Events will also be generated at the base station unit 30 if the memory of the base station unit 30 is full.

As will be explained in detail below, the base station unit 30 is preferably programmable remotely from the remote monitoring station 50 via modem or, in an alternative embodiment, locally using a laptop or PC. In the latter case, the base station unit 30 would have an interface for the optional connection of a PC or notebook computer for the display of graphical data or for programming of the base station unit 30. The local PC or laptop could also be used for a simple video link with the remote monitoring station 50. In any case, programming of the base station unit 30 is password protected. Programming involves setting study start and stop times, setting thresholds and minimum breach times, setting pre-specified dial up times for the remote monitoring station 50 to download data, setting data collection times (e.g., 5 minutes every hour), and setting times for recording data from auxiliary sensors. In this manner, the physician may choose to collect only the required summary data and at intervals set by the physician. If, upon review of the summary data, additional detail is required, then the remote monitoring station 50 may request an immediate data upload containing the desired detail data, if available.

In the preferred embodiment, the remote monitoring station 50 has the ability to automatically dial in to the base station unit 30 to download data at specified times. If the line for the base station unit 30 is busy, the remote monitoring station 50 may also have the automatic ability to try again after a pre-specified period. However, the inventors contemplate that in an alternative embodiment the base station unit 30 could initiate the dial-up for uploading the stored data. Generally, the data is downloaded in a binary TCP/IP compatible protocol, providing guaranteed transmission integrity over the link with the remote monitoring station 50.

In the preferred embodiment, the base station unit 30 has a plug-in for a normal telephone so that the patient is not required to have two telephone lines. Voice communications will take precedence over data communications, i.e. the patient will be able to interrupt a data download if he or she needs to make an urgent telephone call.

C. Remote Monitoring Station

At the remote monitoring station 50, a physician or nurse has access to a normal PC connected by modem to the telephone line 40. Physiological monitoring software is run on this PC or on a networked system to process the data received via the modem from the base station unit 30. Preferably, though not necessarily, the received data will incorporate the serial number of the base station unit 30, as well as the serial number of the sensor band 10, to be used for historical data tracking purposes, should this be necessary. Remote monitoring station 50 may display continuous or non-continuous data, including events data, from a database or other electronic file for review by a physician.

Figure 4A:
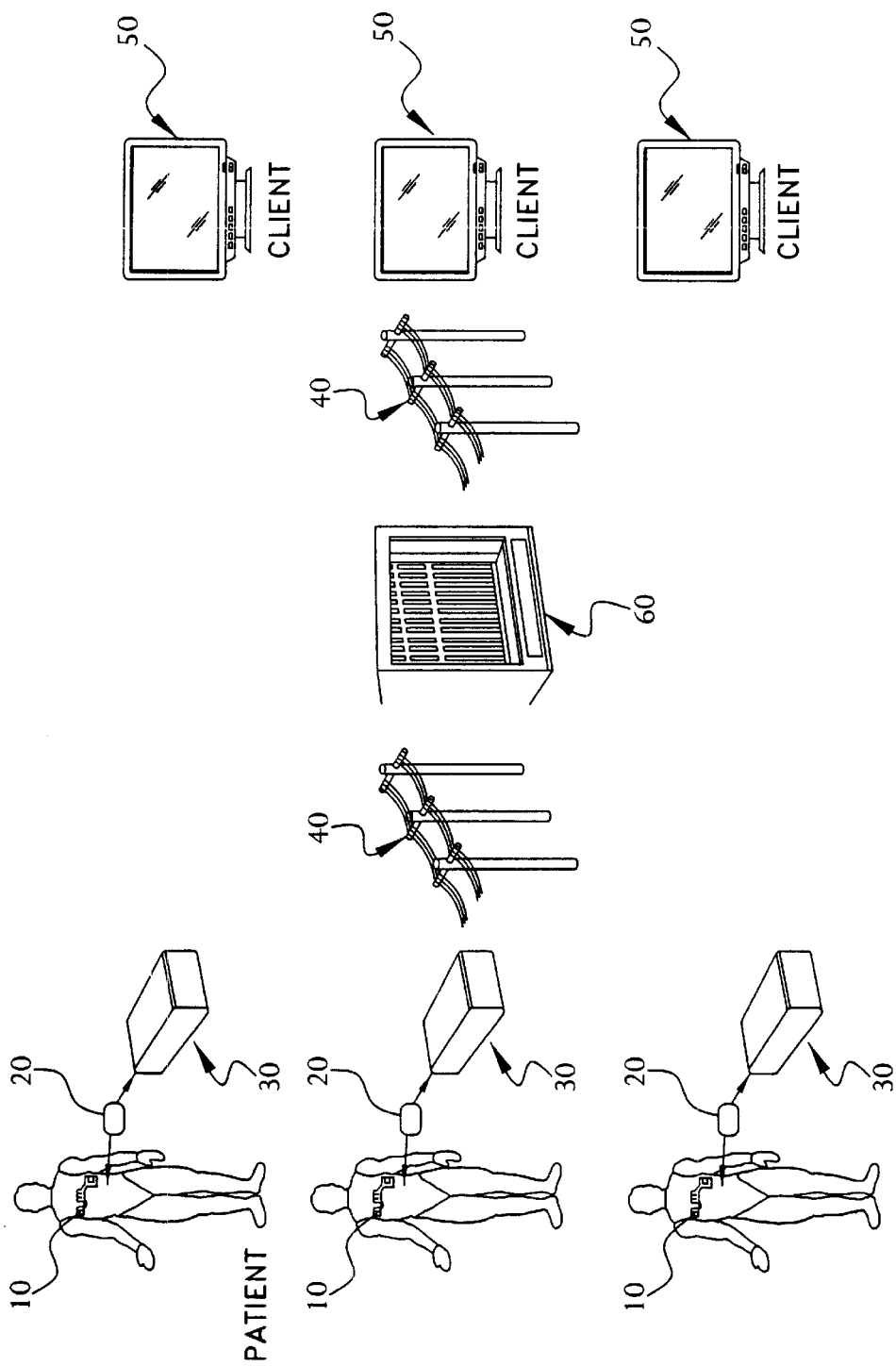
FIG. 4A illustrates a remote monitoring embodiment in which a server is used for data acquisition from a plurality of patients and the acquired data is provided to client systems which are connected so as to access the acquired data for analysis.
Figure 4B:
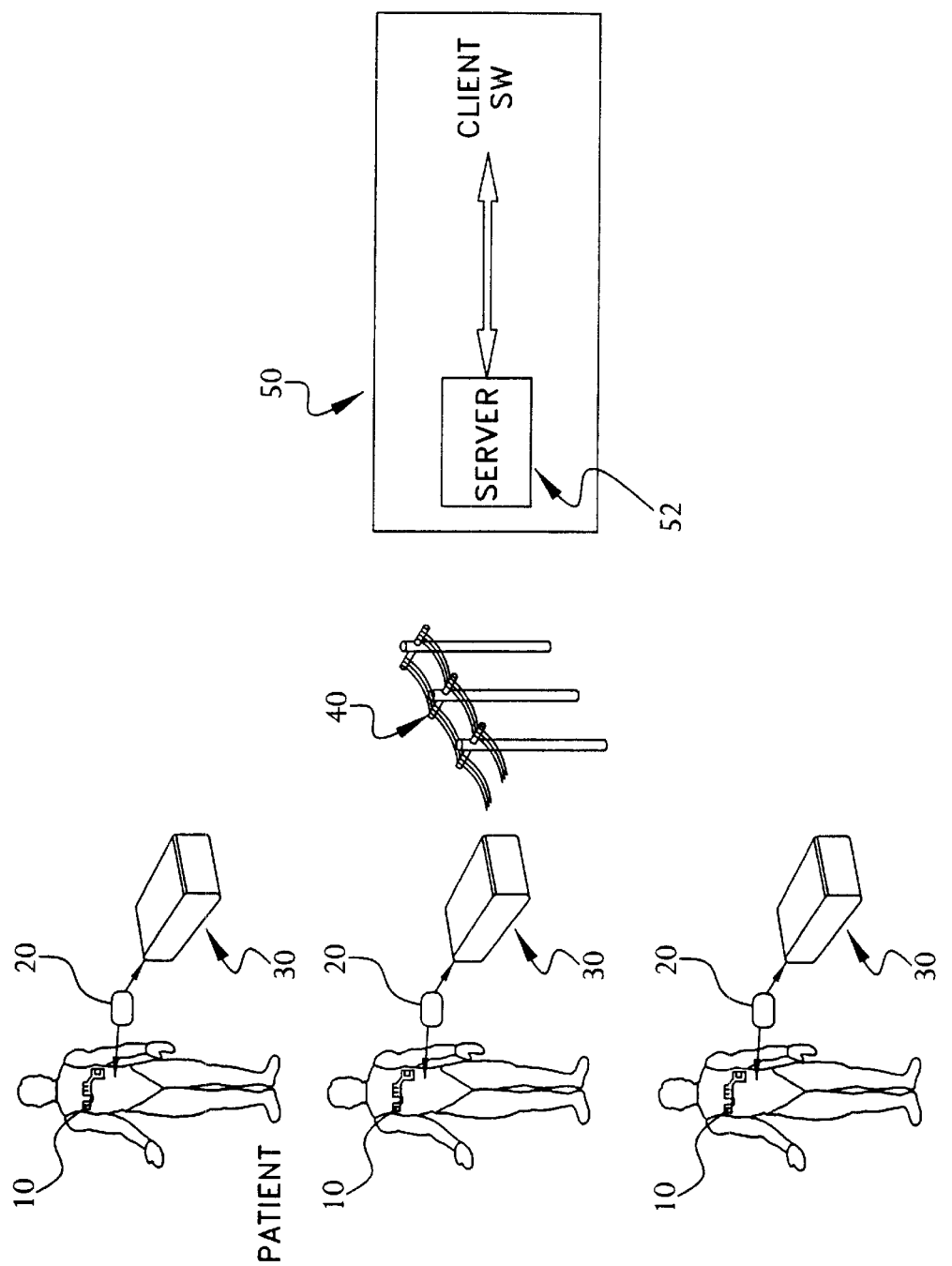
FIG. 4B illustrates a remote monitoring embodiment in which the end user has a server for data acquisition from a plurality of patients, where the end user accesses the server directly.

As illustrated in FIG. 4A, a server 60 may be located in the transmission lines 40 to permit data from a plurality of patients to be stored on the server 60 and provided to a plurality of remote monitoring stations 50 in a telemonitoring center or centers. In this case, a plurality of patients are monitored in accordance with the techniques of the invention and an operator at the telemonitoring center may configure studies and analyze data from many patients. On the other hand, as illustrated in FIG. 4B, the remote monitoring station 50 may be used to simply monitor a single patient or several patients from a single remote monitoring PC running the server 52 and physiological monitoring software.

At the start of any patient study, the operator of the remote monitoring station 50 will need to configure the system's software for the type of study, e.g. historical data viewing, viewing of summaries, etc. The operator will also need to remotely program the base station unit 30 to collect the desired data from the patient. In some circumstances, the operator at the remote monitoring station 50 also may want to dial in to a particular base station unit 30 to check the status of a particular patient. In these instances, the operator will be able to view the vital signs data most recently uploaded from the memory/smart card 20, even if such data is not otherwise scheduled to be downloaded by the base station unit 30 for a particular study. The operator also may download any data that has previously been stored at the accessed base station unit 30. The operator will need to program a unique patient identifier at the start of a study so that data recordings can later be identified and so that patient data confidentiality may be maintained.

The inventors contemplate that the physiological monitoring software could detect threshold violation conditions locally and could alert the operator of the remote monitoring station 50 or of a central monitoring station on a network to this fact.

In a preferred embodiment, the remote monitoring station 50 may display several scrolling traces and several numerical measures on a single screen at any time, with the operator able to configure which traces or measures he/she wishes to see. The operator will be able to choose from a number of time bases for the review of the most recently received or historical data. Some parameters (eg. temperature) could be shown as the latest numerical value only. The operator will also have the ability to define a data schedule enabling him/her to download selected samples of the continuous and auxiliary sensor data to the remote monitoring station 50. When a threshold event is detected by the base station unit 30, a "recording session" for later download may be flagged, causing a block of data to be recorded containing all the parameters being monitored for several (e.g. ten) minutes leading up to the event and for its duration.

If a monitoring station 50 is provided as in the FIG. 4A or 4B embodiments, the remote operator will be able to review data from a number of patients, with data being transmitted from a number of base station units 30. When data is downloaded, events data could be sent first and could be viewed for any particular patient by the operator. The physiological monitoring software enables summaries of data to be viewed, e.g., traces of sample data points taken every 15 minutes for a particular parameter, and a display of events generated. For review of historical data, on the other hand, the physiological monitoring software will enable the operator to look at data using a choice of time-bases and a horizontal scroll bar. Thus, the operator could review the uploaded summaries at the remote monitoring station 50 and determine if more detail is necessary. If so, the remote monitoring station 50 could initiate a data upload of the designated data from the base station unit 30. In a preferred embodiment, the physiological monitoring software contains software algorithms for the analysis of the ECG signal for standard single or multiple lead ECG waveform measurements, interval measurements, beat-typing and for arrhythmia detection. These algorithms preferably include artefact detection and filtering to ensure that a high quality reading is obtained. The algorithms preferably include a 50 Hz/60 Hz notch filter for removal of any mains noise and the above-mentioned 3 lead detection algorithm.

For any data downloaded by the base station unit 30, the data is stored in a standard flat file format on the local hard disk, or in a separate location such as on a separate optical disk drive. In a preferred embodiment, all blocks of data stored are in a form that enables them to be exported from the physiological monitoring software in an HL7 compliant format. Each block of data stored may have a unique patient identifier, the sensor band and base station unit identification numbers, the date, and the time.

Remote monitoring unit 50 may also perform other types of processing on the received ECG data such as heart rate variability analysis, atrial fibrillation detection, ST episode detection, QT analysis, and other flagging events. Such processing techniques may be used to detect disease states such as cardiac failure, hypertension, angina, ischaemia/ coronary artery disease, peripheral vascular disease, acute and chronic respiratory insufficiency, history of recurrent arrhythmias, sub-acute patients, post-infarction patients, acute and recurrent febrile illnesses (including malaria, hepatitis, lymphoma, Hodgkin's disease, AIDS, tuberculosis) and the like, and such processing techniques are believed to be known to those skilled in the art.

II. System Electronics

As noted above, a first embodiment of the present invention stores the vital signs data on a memory/smart card 20 inserted into a memory card connector dock 13 on the sensor band 10 and then reads the stored data from the memory/smart card 20 using a memory/smart card reader 39 at a base station unit 30. Alternatively, the smart card 20 includes transmission electronics for transmitting the vital signs data to the base station unit 30 or to a portable data logger carried by the patient for subsequent download to the base station unit 30. The data stored in the base station unit 30 is then transmitted over conventional phone lines 40 or via a conventional wireless telecommunications link to the remote monitoring station 50.

Figure 5A:
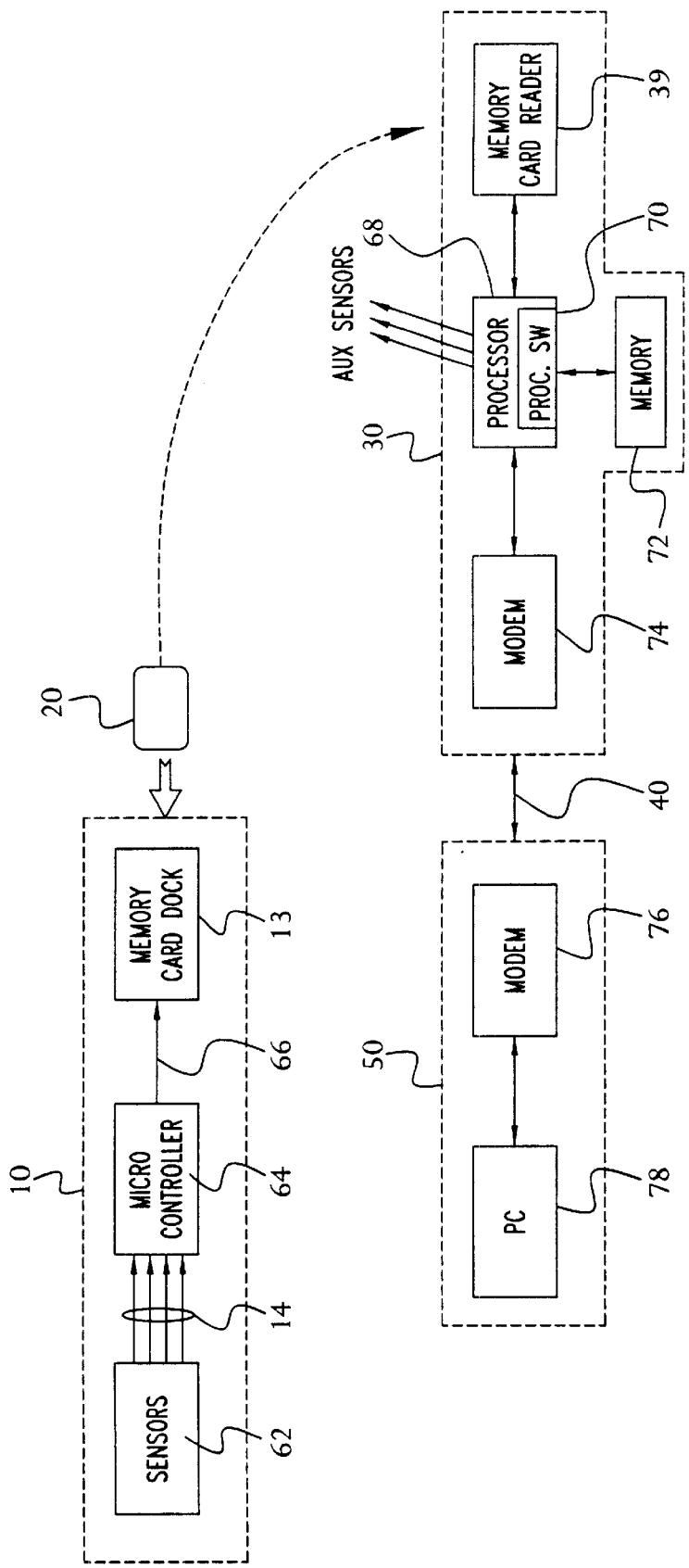
FIG. 5A illustrates a general block diagram of the system electronics in accordance with a first embodiment whereby a memory card stores the vital signs data.

FIG. 5A illustrates a general block diagram of the system electronics in accordance with a first embodiment of the invention. Alternative embodiments will be described below with respect to FIGS. 5B–5D. As shown in FIG. 5A, the sensor band 10 includes a plurality of sensors (e.g., electrodes) 62 which provide analog vital signs data via traces 14 to a microcontroller 64 for A/D conversion and signal conditioning. Microcontroller 64 also provides the necessary supply and drive signals to the electrodes 62. A memory card connector dock 13 accepts the memory card 20 and includes a connector 13' which allows the conditioned vital signs data 66 from the microcontroller 64 to be stored on the memory card 20. Memory card 20 thus receives data from the microcontroller 64 including multiplexed sensor signal sample data. The sensor band 10 continuously stores the data 66 including vital signs data on the memory card 20, and the contents of memory card 20 are later given/mailed to the operator of the monitoring station 50 or inserted into memory card reader 39 of the base station unit 30 for later uploading to the remote monitoring station 50. As noted above, base station unit 30 includes a processor 68 which preferably implements software algorithms 70 that calculate heart rate and respiration rate from the ECG and respiration signals, respectively. The received vital signs data is accumulated in memory 72 where it is stored until a remote monitoring station upload is initiated, at which time the stored data is uploaded over communications link 40 using modem 74 of the base station unit 30 and modem 76 of the remote monitoring station 50. For example, the vital signs data may be uploaded once per day in the early morning hours to minimize interference with normal telephone usage, uploaded several times per day, or once per week. Remote monitoring station 50 then processes and displays the received vital signs data using a conventional personal computer 78, as will be described in more detail in the following section.

In a preferred embodiment, communications link 40 is used to transfer the acquired patient vital signs data from the base station unit 30 to the remote monitoring station 50 and to transfer configuration information from the remote monitoring station 50 to the base station unit 30. In the preferred embodiment, the base station unit 30 and remote monitoring station 50 communicate in a stream-based protocol implemented using TCP/IP sockets, where each data packet has a message start byte, bytes indicating total message length, a message command, and message contents. The data packets generally contain a data timestamp and ECG, respiration, temperature, motion, and bend data; however, data packets from the base station unit 30 may also contain weight, blood pressure, and spirometer readings from the auxiliary sensors. Other packet types may include heart rate, respiration rate, temperature and/or event data.

Generally, before TCP/IP communication between the base station unit 30 and the remote monitoring station 50 can be established, a network connection must first be established between the two systems. The remote monitoring station 50 initiates connection to the base station unit 30, and once the connection has been accepted, both ends of the communications link 40 will listen for commands. The protocol may be terminated by either end of the communications link 40 disconnecting its socket. Each command is unidirectional, and acknowledgment of any command is necessary.

A command set of the protocol for communications between the base station unit 30 and the remote monitoring station 50 in the preferred embodiment of the invention will now be described. The following partial list of commands are used to implement the communications protocol over the communications link 40.

A SetConfig command from the remote monitoring station 50 sends any required configuration data to the base station unit 30 and may contain flags instructing the base station unit 30 to flush the databases of the base station unit 30.

An AckConfig command from the base station unit 30 acknowledges to the remote monitoring station 50 successful receipt of the SetConfig message.

A DataRequest command from the remote monitoring station 50 requests that the base station unit 30 sends a specified time range of raw data to the remote monitoring station 50. The data record type field within the command specifies the format that the remote monitoring station 50 will expect to be returned. In some cases, the same raw data may be requested in multiple formats. Only one request for data may be active at any one time.

A DataRequestAbort command message from the remote monitoring station 50 causes all outstanding data requests to be aborted, including Event and Alarm data requests. This command should be sent before the remote monitoring station 50 terminates the communications link 40.

A ReturnComplete command is sent by the base station unit 30 to indicate that all data for the last data request has now been sent to the remote monitoring station 50. In this context, a data request includes a request for threshold settings, session data, or events. A status field in this command indicates the reason for the base station unit 30 to stop transmission of Return records.

A DataReturn command packet from the base station unit 30 contains data as requested via a DataRequest command. Different data record types will have different data sizes.

A SetAlarm command from the remote monitoring station 50 is used to set up a threshold alarm monitor on the base station unit 30. A duration parameter indicates for how many seconds the threshold must be exceeded before the alarm is triggered. A hysteresis parameter defines a boundary around the threshold that needs to be crossed before the alarm triggers or resets.

An AlarmDataRequest command from the remote monitoring station 50 requests that the base station unit 30 send all alarms recorded between the Start and End times supplied. The data actually is returned as a series of "Alarm" commands, followed by a ReturnComplete message.

A RemoveAlarm command from the remote monitoring station 50 causes the base station unit 30 to stop monitoring for the specified alarm. This command can only be used to stop monitoring for an alarm that was configured using the SetAlarm command.

An Alarm command packet from the base station unit 30 encapsulates an alarm and returns an Alarm ID to the remote monitoring station after the SetAlarm message.

A SetEventMeasurement command message from the remote monitoring station 50 requests that the base station unit 30 makes an auxiliary measurement. If the alert time is outside the range defined by the start and end times, no user alert is sent. If a periodic flag is set, the measurements are made daily, and the date portion of the start, end, and alert times are ignored.

An EventReading command from the base station unit 30 contains the results of a scheduled auxiliary measurement, as requested by the SetEventMeasurement command. Data valid flags are used to indicate the nature of the data contained in the measurement.

An EventDataRequest command message packet from the remote monitoring station 50 contains a request for event data specified for the specified time range. The response is a series of EventReading command packets followed by a single ReturnComplete command.

A TestRequest command is sent by either end of the communications link 40 and is used to test the link between the two systems. A TestRequest command should result in a TestResponse packet within 3 seconds in a preferred embodiment.

A TestResponse command packet is sent in response to the TestRequest command packet and may include a copy of the data accompanying the TestRequest message.

Of course, other commands may be added as system features are added. Moreover, it is desired that the vital signs data be compressed for faster data downloading to the remote monitoring station 50.

Alternatively, the memory card 20 may be mailed or returned to the remote monitoring station 50 for reading at the remote monitoring station 50.

Those skilled in the art will appreciate that the memory/smart card 20 may function as an on-body data logger preferably having enough memory to last 24 hours (i.e., until the sensor band 10 is changed). This embodiment stores the collected sensor data locally on the memory/smart card 20 for downloading to the base station 30 upon completion of the daily monitoring session. Another memory/smart card 20 would be used with the next sensor band 10 while the contents of the first memory/smart card 20 are being downloaded. This embodiment simplifies the downstream electronics and removes the need for any form of wireless communications between units, thereby providing a fully ambulatory system with no range limitations. However, this freedom of movement is traded off against an increase in size and weight of the memory card 20 (approximately 2.5 times the size of a wireless circuit at around approximately 80 square centimeters and 100 grams) and a requirement of tightly integrating the electronics to minimize the size of the smart card 20 and to reduce power consumption.

The embodiment of FIG. 5A also precludes an option for real-time monitoring and thus does not provide a "live view" of the patient's data from the remote monitoring station 50. The embodiment of FIG. 5A also reduces the ability to check sensor location, thus requiring users to verify the addition of additional views prior to monitoring.

Figure 5B:
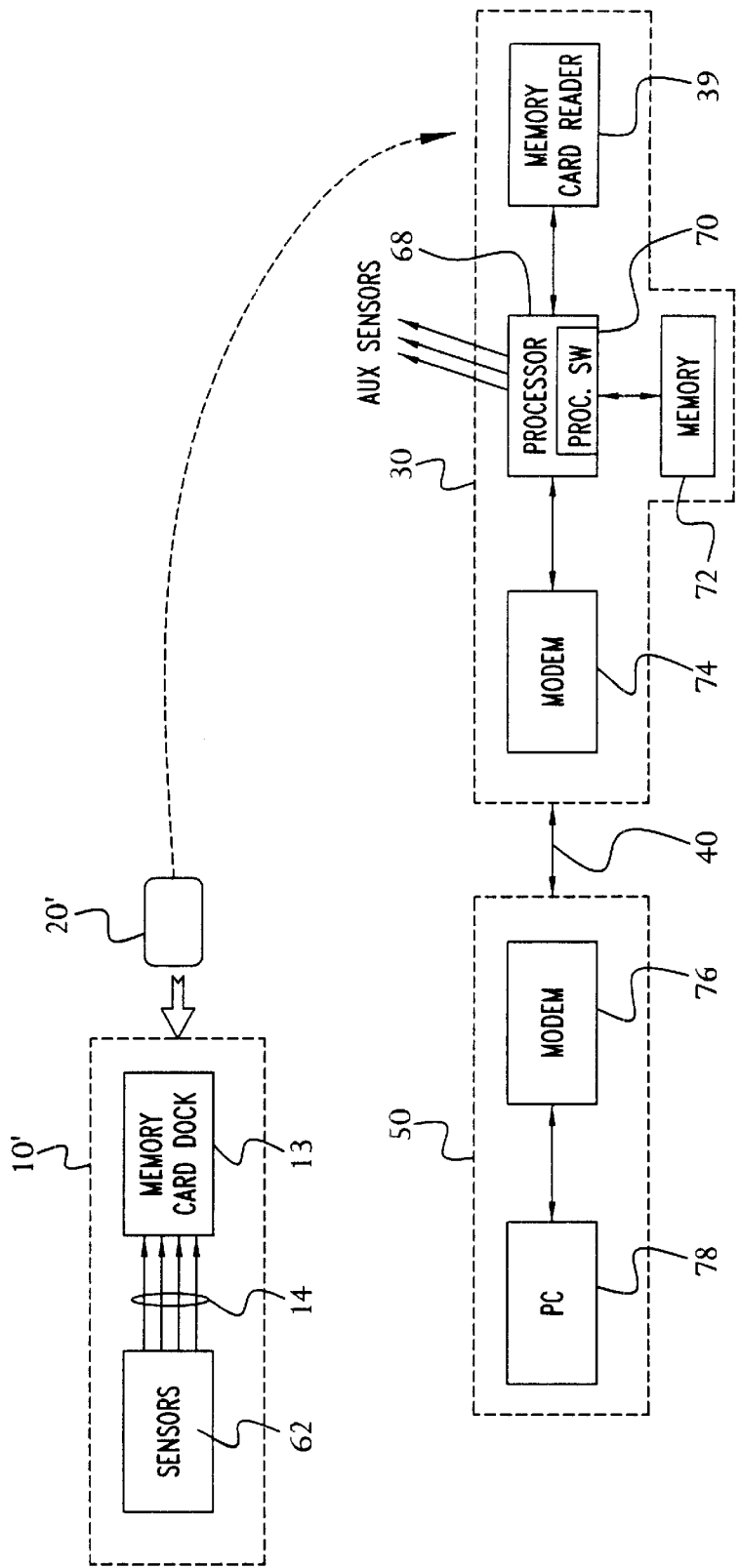
FIG. 5B illustrates a general block diagram of the system electronics in accordance with a second embodiment whereby a smart card stores the vital signs data and also includes the sensor electronics.

In an alternative embodiment, the signal processing circuitry 12 including microcontroller 64 and the associated battery/power components may be included on the smart card 20' as shown in FIG. 5B. In this embodiment, the signal processing circuitry 12 as well as the memory of the smart card 20' may be reused by respective sensor bands 10', thereby minimizing the cost of the disposable sensor bands 10'. As noted above, the battery/power components need not be on the smart card 20' but may be included in the sensor band 10'. This embodiment also has the same benefits and detriments as the embodiment of FIG. 5A except that it has the added benefit that all electronics are reusable, thereby minimizing cost of the disposable sensor band 10'.

Figure 5C:
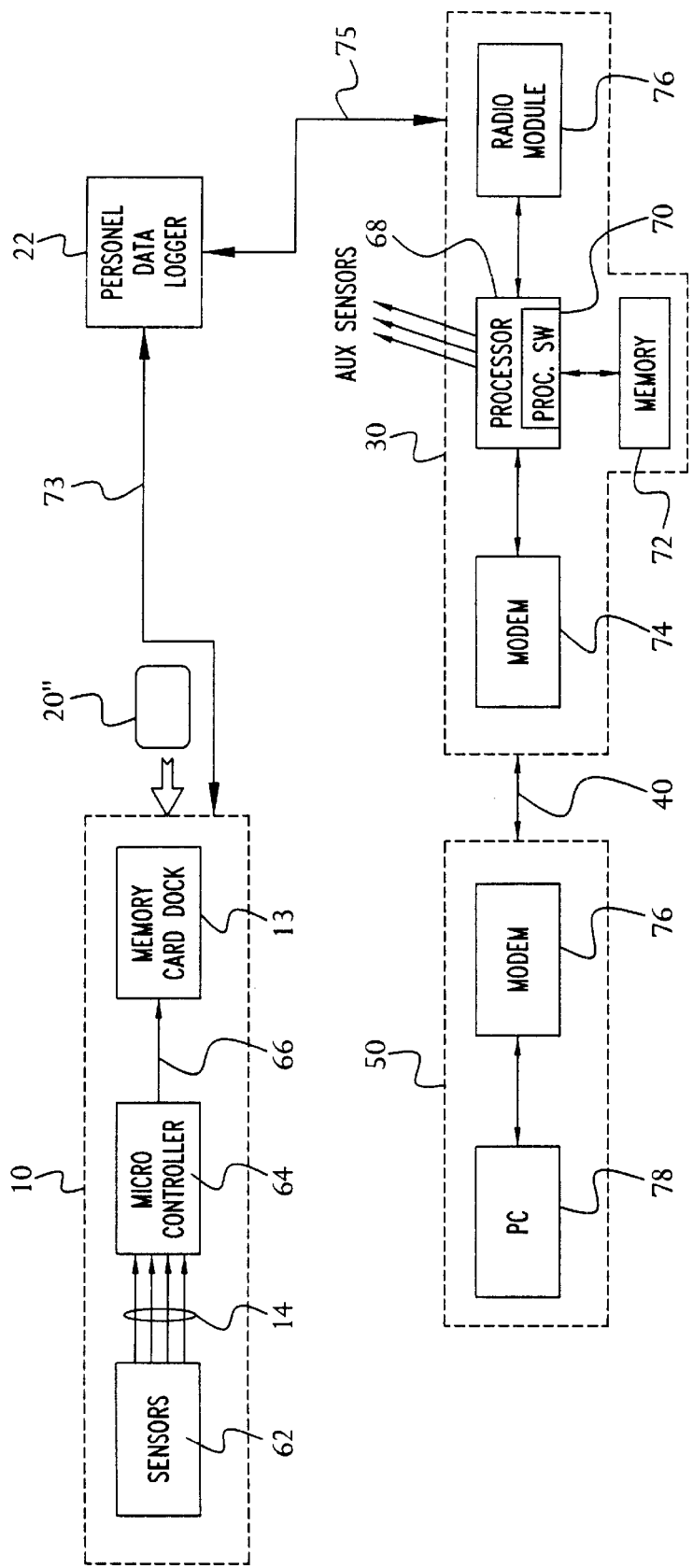
FIG. 5C illustrates a general block diagram of the system electronics in accordance with a third embodiment whereby the smart card includes reusable electronics for broadcasting the vital signs data to a personal data logger where the data is stored and/or retransmitted to the base station unit.

In yet another embodiment illustrated in FIG. 5C, the signal processing circuitry 12 may be included on the smart card 20" along with microcontroller circuits and transmitter elements that transmit the vital signs data over a one or two-way communications path 73 to a nearby portable data logger 22 of the type described in commonly owned U.S. patent application Ser. No. 09/292,405, filed even date herewith. As shown, the personal data logger 22 in turn communicates over one or two-way communications path 75 with radio module 76 of the abase station unit 30. Though not shown, the base station unit 30 in this embodiment may also have a memory/smart card reader 39 as in the embodiments of FIGS. 5A and 5B. This embodiment allows for reuse of the signal transmission circuitry and power supply from one sensor band 10 to the next while otherwise keeping the system functionality described in detail inthe above-reference parent application, U.S. patent application Ser. No. 09/292,405, filed Apr. 15, 1999. As in the embodiments of FIGS. 5A and 5B, the battery/power components need not be on the smart card 20" but may be included in the sensor band 10.

Figure 5D:
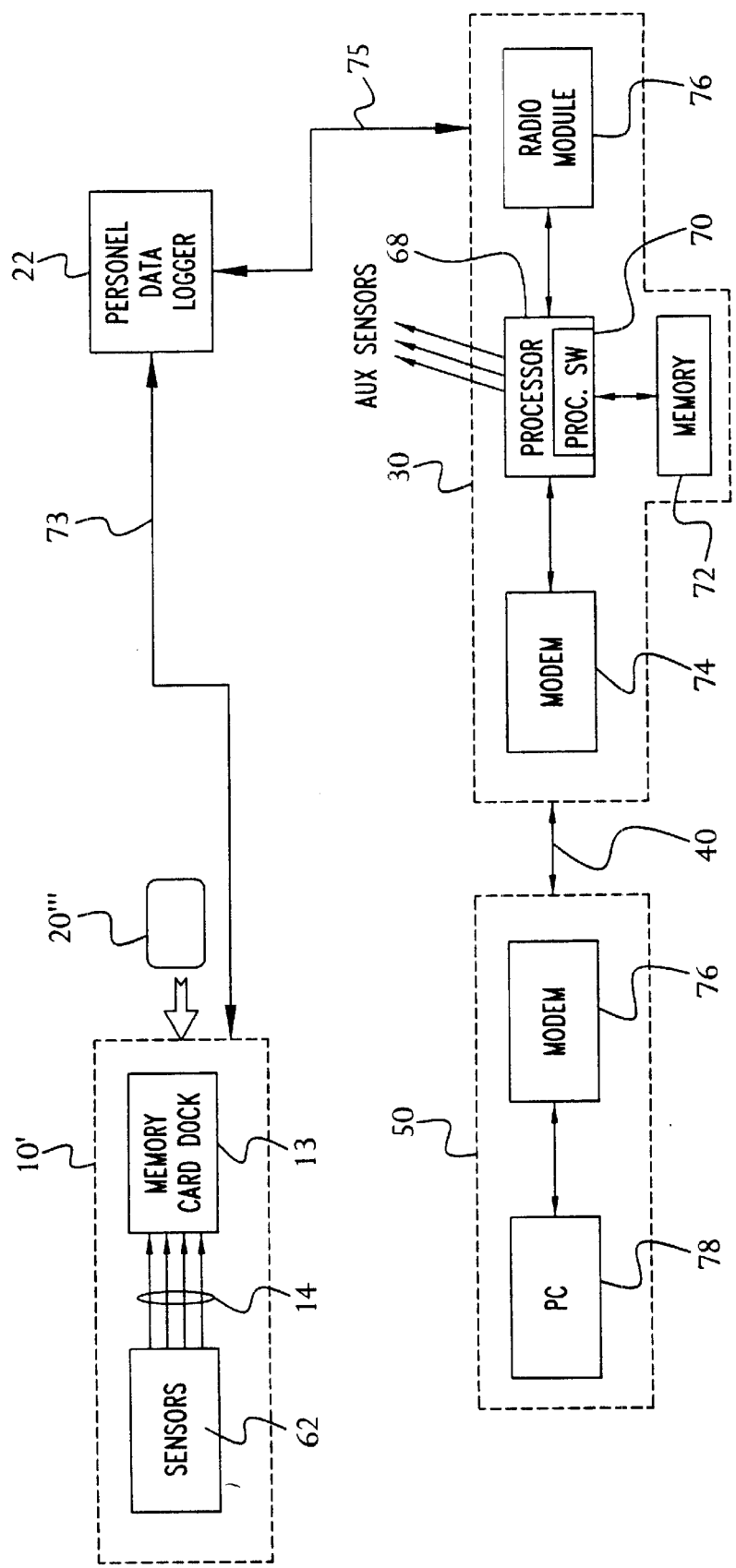
FIG. 5D illustrates a general block diagram of the system electronics in accordance with a fourth embodiment whereby the smart card includes the sensor electronics in addition to the reusable electronics for broadcasting the vital signs data to a personal data logger.

Alternatively, in what is currently a preferred embodiment, the signal processing circuitry including microcontroller 64 and the associated battery/power components may be included on the smart card 20'" along with the signal transmission circuitry as shown in FIG. 5D. The embodiment of FIG. 5D is otherwise the same as the embodiment of FIG. 5C. As noted above, the battery/power components need not be on the smart card 20'" but may be included in the sensor band 10'.

In the embodiments of FIGS. 5C and 5D, the smart cards 20" and 20'" enable a one-way wireless limited range transmitter for transmitting vital signs data from the sensor band 10 to a personal data logger 22 kept on or near the patient (typically within 10–15 meters). Though a base station unit 30 is not required, these embodiments also have the option of adding the base station unit 30 for applications requiring the use of auxiliary sensors and/or remote access to the vital signs data (i.e., two-way transmission for the acquisition of live data). These embodiments allow the electronics on the smart card 20" or 20'" to be minimized to a much smaller weight and area (approximately 12 square centimeters and 30 grams in an exemplary embodiment) but requires the addition of the portable data logger 22 to store the vital signs data. In simple applications, the portable data logger 22 operates as a miniature portable base station but must be carried by the patient if the patient wishes to go further than 15 meters from a dock in the base station unit 30 adapted to accept the portable data logger 22 for data download as described in the afore-mentioned related application. Off the shelf wireless technology options may be used for the wireless transmissions. In a presently preferred embodiment, a simple FM transmitter using the low power unlicensed band of 868 MHz/916 MHz is used to provide a two-channel system to allow some flexibility in using systems in close proximity (30 meters) as in a hospital setting. Because of the reduction on space and power constraints in the portable data logger 22, it is further possible to increase the functionality of the portable data logger 22 to include basic heart, respiration, and pulse oximetry calculations and an LCD display for display to the patient of the patient's vital signs data waveforms in real-time.

Those skilled in the art will appreciate that the data storage requirements of the system are significant, with uncompressed data storage of 24 hours of vital signs data requiring around 140 Mbytes at the sampling rates described herein. Data compression is preferably used; however, data compression is limited to small rations such as 1.5 to 1 due to the processing power required of the sensor band electronics or the electronics of the portable data logger 22. Accordingly, it is currently contemplated that at least 96 Mbytes will be required for the memory card 20 or smart card 20' in the embodiments of FIGS. 5A and 5B or for the portable data logger 22 in the embodiment of FIGS. 5C and 5D. Of course, the portable data logger 22 could include a digital signal processing (DSP) unit which could allow for a much higher level of compression with a corresponding cost saving in memory size.

Also, the transmission circuitry of the smart card 20" or 20''' preferably inserts an identifier stored in an onboard EEPROM in order to identify the source of origin of the transmitted vital signs data. A session number may also be included in each transmitted data packet for use by the personal data logger 22 to differentiate between monitoring sessions.

III. Collecting/Managing Data Using Remote Monitoring Station

A. Monitoring Software

Figure 6:
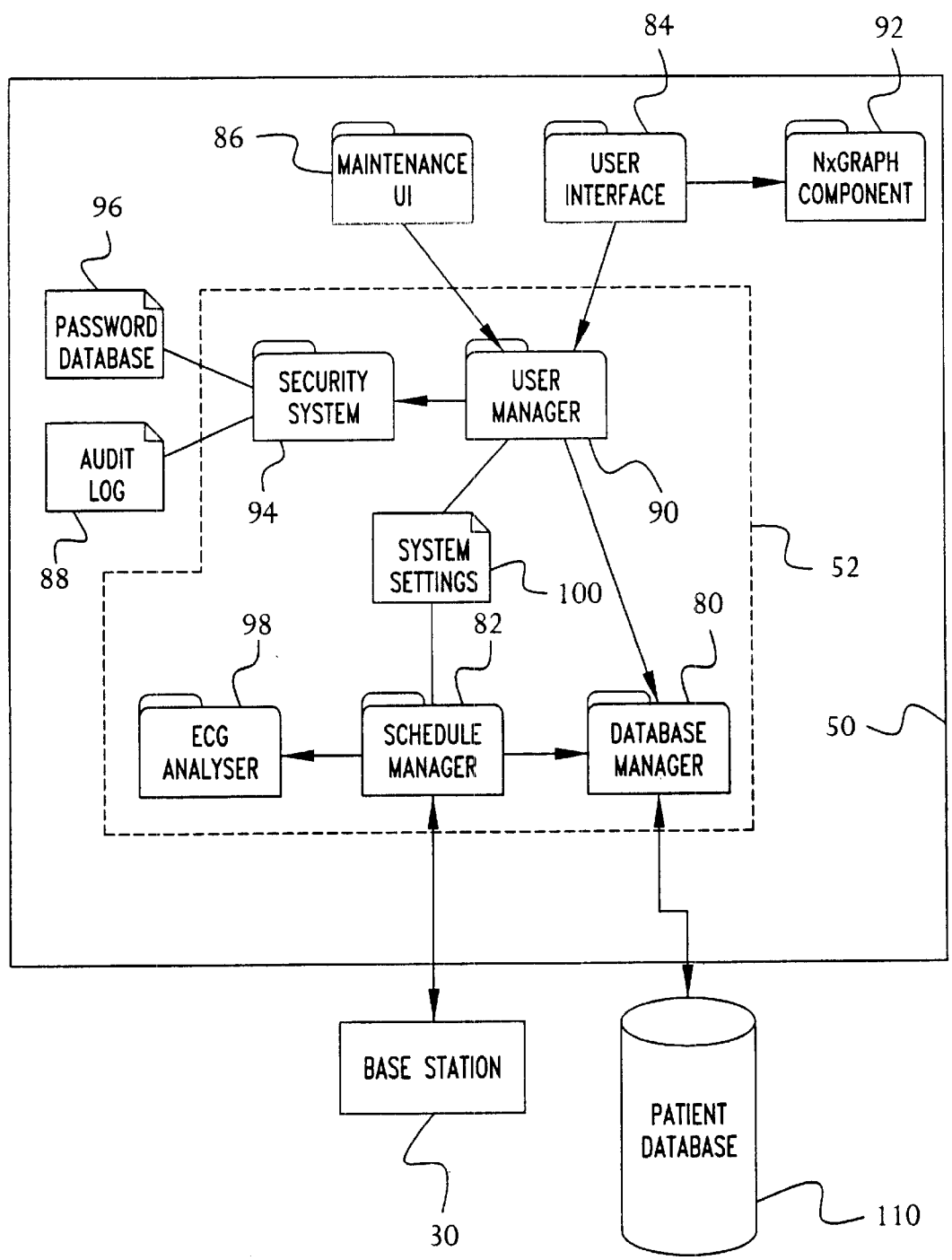
FIG. 6 illustrates the architecture of the software of the remote monitoring station.

FIG. 6 illustrates the functional or software architecture of the remote monitoring station 50. As noted above, remote monitoring station 50 is utilized by a health care professional to evaluate the vital signs data received from one or more patients and to perform control functions and maintenance functions necessary for system operation. FIG. 6 illustrates an embodiment of FIG. 4B in which the remote monitoring station 50 includes a server 52 for managing the processing of the vital signs data received from the base station units 30. A similar functional arrangement would be utilized for implementing the embodiment of FIG. 4A except that the server would be located in a separate physical unit or at a remote location. Each of the components of FIG. 6 will now be discussed in turn.

The remote monitoring station 50 maintains a database 100 of patient data received from each patient taking part in a study using the techniques of the invention. In a preferred embodiment, the patient data includes a patient number which is unique for possibly linking to other patient information systems and a telephone number for the patient's base station unit 30. Preferably, additional information is maintained for each patient case which is linked to the patient information. Such information may include current medications taken by the patient, current diagnosis information, base station ID, settings used to obtain data from the base station unit 30 and auxiliary sensors, and the like.

The software of the remote monitoring station 50 maintains the patient database 110 and allows the operator to access such data for analysis and processing. As illustrated in FIG. 6, database manager 80 manages all interactions with the patient database 110. Database manager 80 runs as a continuous background process to ensure that data can always be stored on arrival. The main interface is with the database management system used for the patient database 110; all other interfaces involve extraction of information from the patient database 110.

Schedule manager 82 is responsible for all interactions with the base station unit 30 and, like the database manager 80, runs continuously as a background process. Since information about the required schedules for patient studies is stored in the patient database 110, the schedule manager 82 must obtain all relevant schedule information from the database manager 80. Similarly, the schedule manager 82 passes all data to be stored (i.e. case session data, case alarm data) to the database manager 80 for storage in the patient database 110. The schedule manager 82 interfaces with the rest of the system through the database manager 80. The schedule manager 82 also needs to interface to any modems used to connect to base station units 30. Schedule manager 82 further implements the base station-remote monitoring station communications protocol described in the previous section.

The main user interface 84 provides all normal user interaction with the remote monitoring station 50. In the preferred embodiment, the user interface 84 has no customization or set-up options; all such functionality is provided by the system maintenance user interface 86. User interface 84 is designed to interface with the user manager 90, which maintains current state information and the like. However, some components may interact via different routes for efficiency if this is felt necessary (e.g. the schedule manager 82 may interface directly). Preferably, the user interface 84 embeds instances of the graphics control process 92 for controlling the display of graphical data.

The system maintenance user interface 86 provides control over any configurable parameters. In the preferred embodiment, an interface to the audit log 88 is provided from the system maintenance user interface 86 so that the operator may view the audit log. Preferably, settings that cause changes in visual elements (e.g. graphs) will provide a preview so that the user does not need to keep switching between the two modes. System maintenance user interface 86 also interfaces with the user manager 90 which maintains state information and the like.

User manager 90 maintains state information about a single client user session. The coupling of user manager 90 to user interface 84 depends on the implementation methods actually used. Preferably, user manager 90 obtains a user name and password from the user and then activates either the user interface 84 or the system maintenance user interface 86 depending on the privilege level of the user. User preferences and other settings are read from the system settings object 100. The user manager 90 also accepts connections from graphics objects 92 and supplies the necessary graphical data on demand.

The security system 94 maintains a secure database of user names and passwords used to access the system. There are two levels of user: user and administrator, which are mutually exclusive. In the preferred embodiment, the security system 94 maintains the user database files in an encrypted format. The user manager 90 validates users via password database 96 before continuing using a query to the security system 94.

Finally, an ECG analyzer 98 is provided to analyze in one second chunks any ECG signals passed to it. The processed data is output in a form that can be stored back in the patient database 110 Generally, the ECG analyzer 98 processes data as a complete session. ECG analyzer 98 preferably interfaces to the database manager 80 to perform the ECG analysis and to flag events in the vital signs data as it is uploaded. Generally, the ECG analyzer 98 performs arrhythmia analysis by searching for ventricular fibrillation (VF) and/or typing QRS complexes as normal, ventricular ectopic beat (VEB), SVEB, or artefact. ST analysis may also be performed to check for ST segment elevation, depression, and the like.

If an arrhythmia event is found by ECG analyzer 98, the operator may choose to upload additional patient data around the arrhythmia event, send a warning message to the patient via the communications link 40 to the bases station unit 30 to cause a buzzer on the base station unit 30 to sound, or the patient may be called in for evaluation. Generally, since the review is typically performed several hours after the data is collected, the event is noted and the patient is contacted off-line.

Other functions of these software components may include the following:

1. Scheduling Data Acquisition

Scheduling of downloads, and actual data downloads may well occur at different times. In addition, a system may be managing many patients, yet only has access to a single phone line. Therefore, this aspect of the system will behave independently from the user interface.

Generally, download schedule manager 82 will use the case properties to download data from the patient base station units 30. The information that the user can specify for a patient's schedule is as follows:

| | |
|---|---|
| Monitoring days | The days of the week on which monitoring is to occur |
| Monitoring times | Either 4 specific times of day that monitoring will occur, or a periodic interval (e.g. 6 hours) and a starting time. |
| Monitoring duration | How long to monitor per session |
| Download days | The days of the week on which downloads are to be performed |
| Download time | The time at which a download should be performed |

The download schedule manager 82 should be aware of the download bandwidth available to it, so that estimates of download times can be presented to the user. This can be refined based on actual data transfer times experienced by the system.

Preferably, the download schedule manager 82 will support multiple modems. If multiple downloads are scheduled for the same time, the download schedule manager 82 will order them and perform downloads sequentially (or in parallel if multiple modems are present). Any downloads that fail should be moved to the end of the queue, and retried up to 3 times before failure is reported. Also, any downloads requested immediately by the user preferably will take priority over previously scheduled events, and the user warned of this fact. However, if the data requested does not exist on the base station unit 30, the fact will be audited, and an event raised for that patient, which would be reviewable with all other events on request. If the download is happening interactively, the user will also be notified with a message on the display screen of the remote monitoring station 50. In addition, it is preferred that any data download shall not cause data to be removed from the base station unit 30 such that the same or additional data could be downloaded more than once if necessary (e.g, in the event of a hard disk failure on the remote monitoring station 50 or in the case of a patient informing a physician that he or she felt poorly during the monitoring period at a time for which the data was not scheduled to be downloaded). As noted above, ECG analysis may be performed automatically upon data download, if appropriate.

2. Flagging Events

The following types of event can be set by the remote monitoring station 50 to be flagged by the base station units 30:

| | |
|---|---|
| Temperature threshold | Both high and low, plus an optional time before trigger value |
| HR threshold | Both high and low, plus an optional time before trigger value |
| RR threshold | Both high and low, plus an optional time before trigger value |
| Data not available | Data has been requested by the remote monitoring station 50 that does not exist on the base station unit 30 |

The above events will be stored on the base station unit 30, and new events will be downloaded whenever the remote monitoring unit 50 and base station unit 30 connect.

In addition, the following events will be flagged by the remote monitoring station 50 once data analysis has been performed:

| | |
|---|---|
| BP threshold | Both systolic and diastolic, high and low |
| VEB frequency | as calculated |
| Tachycardia | Onset and finish |
| Bradycardia | Onset and finish |
| Ventricular Tachycardia (VT) | Onset and finish |
| Ventricular Fibrillation (VF) | Onset and finish |
| Asystole | Onset and finish |

3. Data Analysis

The following channels of data may be analyzed: ECG (for both full analysis and heart rate calculation) and respiration (either respiration or bend channels, to produce a measurement of respiration rate). All data analysis is performed automatically on a session whenever results are required, and the results of the data analysis are stored in the patient database 110.

4. Security

For purposes of accountability, and to simplify the user interface for normal users, it is necessary to identify all users with a user name and password. There are two privilege levels: user and administrator. The two levels are mutually exclusive so that it is always necessary to log in as a different user to perform administration tasks. This prevents a normal user from simply giving themselves administration privileges and accidentally changing or accessing certain features.

5. Auditing

It is necessary to audit certain actions performed by the system or by users. The audit record should be kept in audit log 88 (FIG. 6) separate from the patient database 110. Clearing the audit log 88 will only be possible by administrator level users.

A checksum based on file size and modification date is kept in the system configuration, preferably encrypted. If on software start up, the checksum does not match the file, the software should refuse to start until reset by a user with privileged access. In other words, the software will not start until the password is entered. This event will then be logged into the audit log 88. The audit log 88 will consist of entries showing the type of entry, time of occurrence, and the name of the user causing the auditable event (where appropriate). Other event-specific information may optionally be added.

1. Addition of a patient case;
2. Closing a patient case;
3. Re-opening a case;
4. Modification of case properties;
5. Session download;
6. Events triggered;
7. Setting/changing of event settings;
8. Failures to connect to base station units 30;
9. Errors reported by a base station unit 30;
10. Audit log tampering;
11. Data export/import;
12. Data back-up/restoration/archiving; and
13. Adding/removing users.

B. User Interface to Monitoring Software

Figure 7:
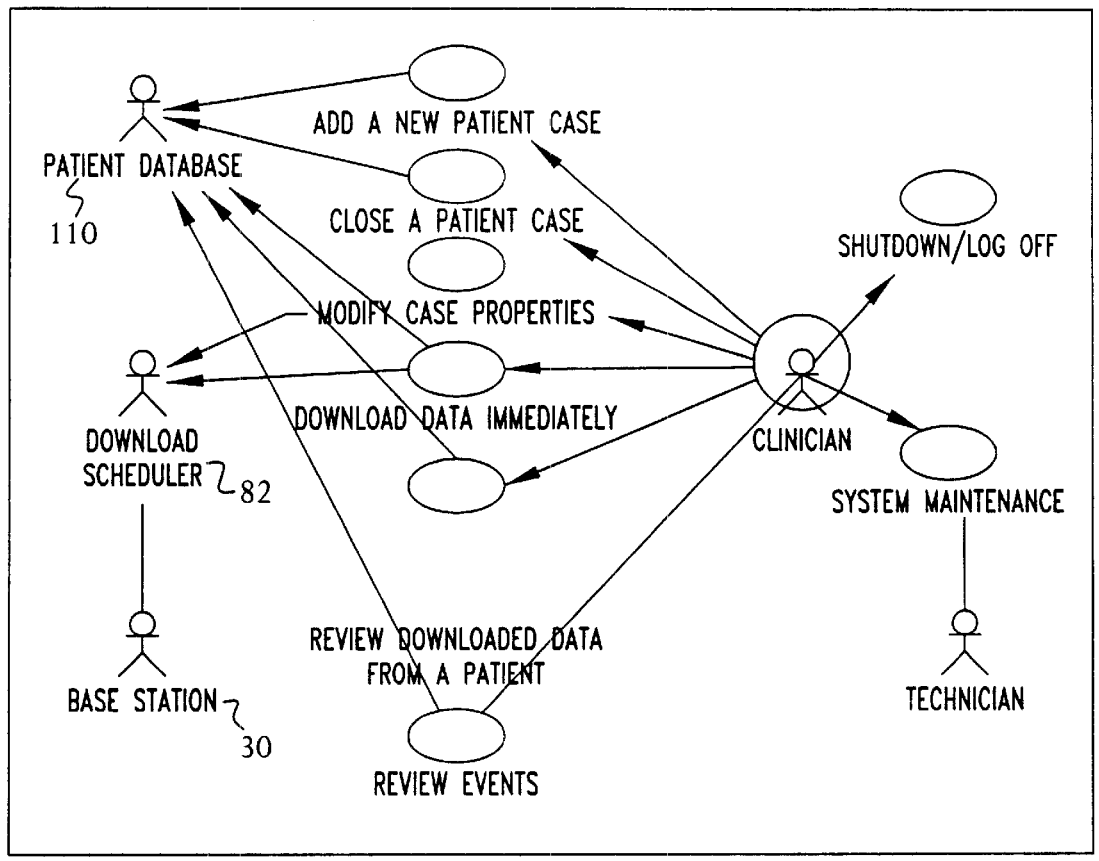
FIG. 7 illustrates a diagram of the top level uses of the remote monitoring station of the invention.

FIG. 7 illustrates a diagram of the top level uses of the remote monitoring station 50 of the invention. As illustrated, such uses include: adding a new patient to be monitored (creating a new patient case), modifying case properties, closing a patient case, downloading data immediately, reviewing downloaded data from a patient, reviewing events, performing system maintenance, and shutting down/logging off the remote monitoring station 50. The use cases and the user interface of the remote monitoring station 50 used for implementing such use cases will be described in this section. Generally, the remote monitoring station's software communicates with the base station unit 30 via the base station/remote monitoring station protocol described above.

Add a New Patient

For this case, the user is prompted to enter the new patient information, with access to all fields in the patient database 110. On finding a duplicate patient number (not name, as there may be people with the same name in the same system), the user is prompted to either try again, create a new case for that patient or go to Modify Case Properties to modify the current case for that patient. If the patient has closed cases, the option is also given to re-open a case. The patient information is added to the patient database 110 if the patient is a new patient, and the case information is also added to the patient database 110.

Modify Case Properties

Figure 8:
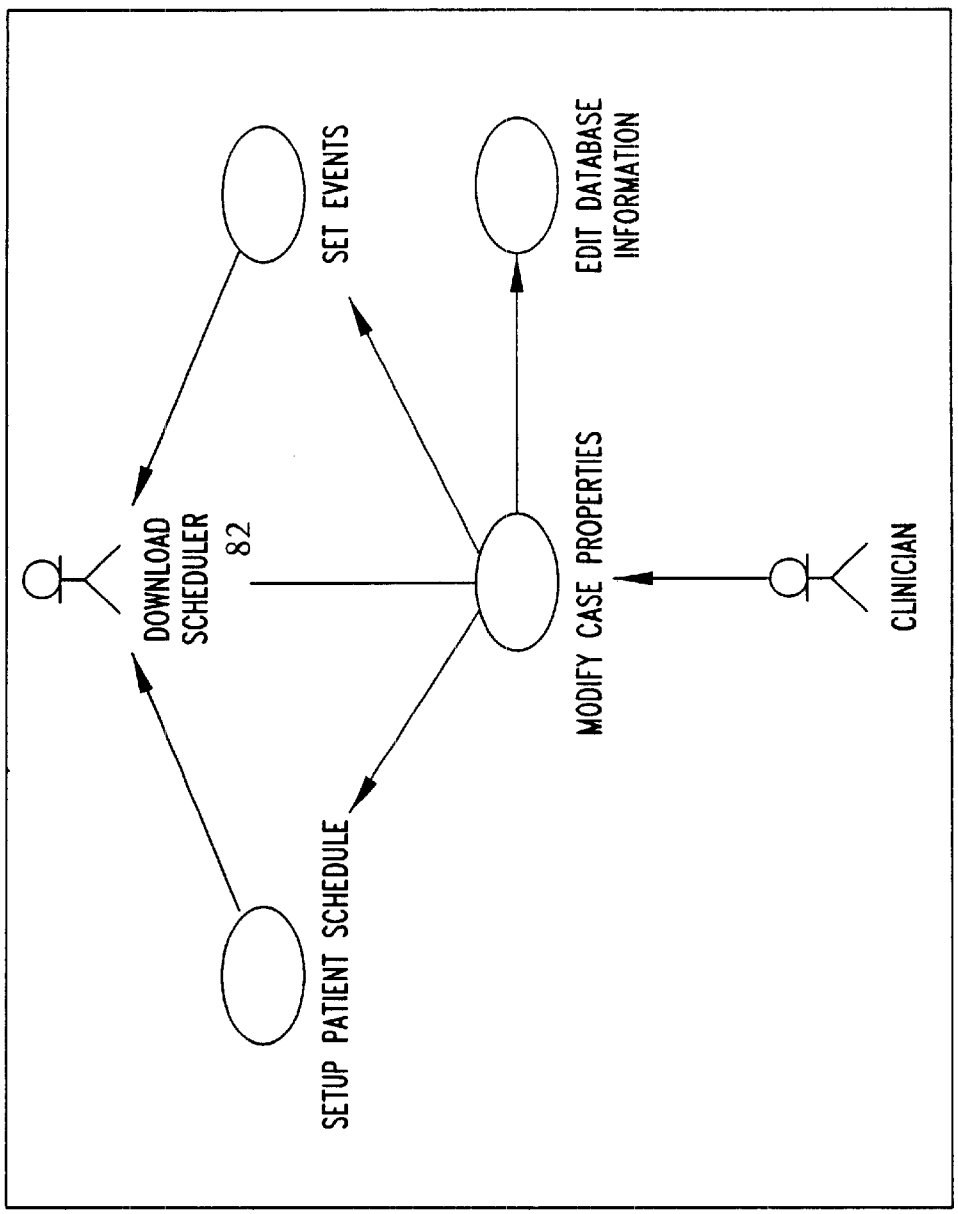
FIG. 8 illustrates the modify case properties process implemented by the monitoring station of the invention.

The user selects the case to modify, and, as illustrated in FIG. 8, the process then splits into the following tasks:

1) Edit Database Information

The user modifies any of the entries in the patient or case record, except the Patient Number and any auto-generated ID fields used to link databases together.

2) Set-up Patient Schedule

This page offers the option to have a look at the current status of the patient. The download properties are entered, with about 3 common defaults accessible from a simple interface, and the current settings (if any) displayed. Some types of download schedules actually result in multiple download instructions being generated, e.g. for downloading 5 minutes per hour over the course of a 24 hour period, with the actual download saved up for a later time. Preferably, download properties are validated, and any conflicts resolved (e.g. if an impossible amount of download time is required). The download properties are then sent to the download scheduler 82. Since some downloads may take an extended period of time, it is desirable that an estimate of the online expected time should be presented when setting download schedules.

3) Set Events

A page showing all possible event types is presented. If none has been set for the current case, all events default to OFF. Each type of event has default parameters that are supplied when it is activated. The events set for this patient case is saved in the patient database 10 with other download information. Changes to the alarm set are audited. Also, each event has associated with it a property that determines if any associated data for a given event is to be downloaded; this specifies the number of minutes data before and after the event to be acquired. This is determined by the remote monitoring station 50, so that the decision to download a session corresponding to an event is made only once an event has arrived at the remote monitoring station 50.

4) Set Auxiliary Sensor Measurements

In a preferred embodiment, the following auxiliary sensors are supported by the base station unit 30: blood pressure (systolic, diastolic and mean), spirometry (FEV1 and PEF), and weight. Measurements are set on an case by case basis; a typical scenario might require 4 measurements per day. A measurement window is defined outside of which the measurement is not made. Optionally an alert point (in minutes before the end of the measurement period) is selectable, which causes the patient to be reminded by the buzzer of the base station unit 30. When multiple measurements are required during the same time window, the order in which the patient is required to make measurements is controllable.

Close a Patient Case

The user is asked to confirm that the case should be closed.

Download Data Immediately

Once the user selects a patient case, the user selects the time range of data to download. The user should be warned if this download would conflict with any others currently scheduled or taking place.

Review Downloaded Data

Figure 9:
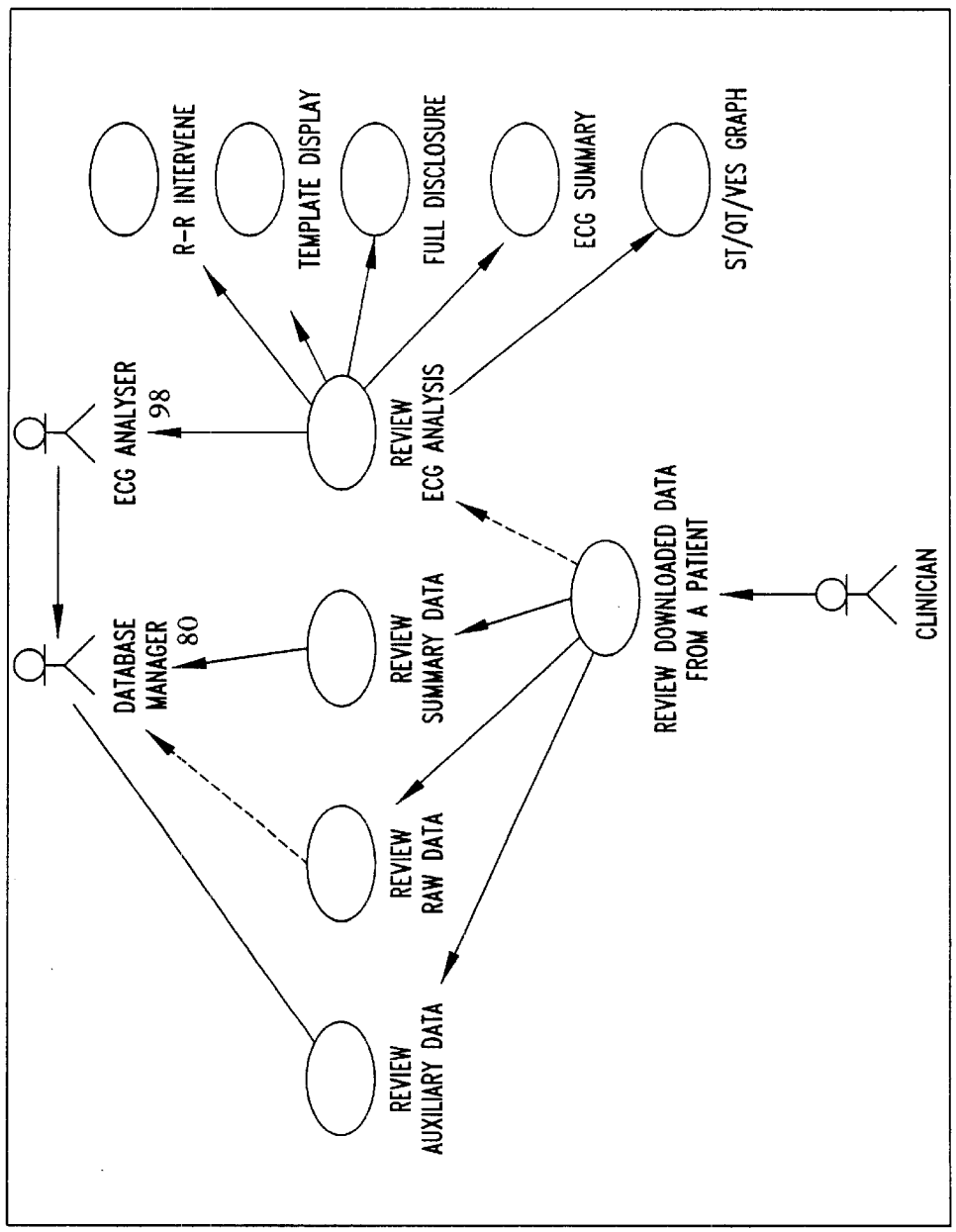
FIG. 9 illustrates the "review downloaded data from a patient" process implemented by the monitoring station of the invention.

FIG. 9 illustrates this use case and its associated subtasks, each of which will be described in turn.

1) Review Raw Data

Once the user selects a patient case, the default display shows ECG, respiration, motion and bend data, with numerical values for heart rate (HR), respiration rate (RR) and temperature. The raw data channels are filtered for display purposes only (filtered data is not stored), and the display time base is selected from 5 seconds, 10 seconds, 20 seconds or 25 mm/sec. Any gaps in the data are shown as gaps in the graphs. System maintenance allows scales to be changed, traces to be added or removed, and colors to be changed. The user has controls to change the time base, to scroll backwards or forwards through the data, to pause the display, to stop monitoring and disconnect from the base station unit 30, and to print the current screen. User controls include the option of turning the above dynamic scrolling on and off.

2) Review Summary Data

Once the user selects a patient case, data is shown as a page of graphs from the whole session, showing HR, RR, and temperature. The display time base is selectable from 30 minutes, 1 hour, 3 hours, 6 hours, 12 hours and 24 hours. Where the session is smaller than some of these ranges, not all options are available (e.g. 24 hour time base is not available for a 1 hour session). Any gaps in the data are shown as gaps in the graphs. Also, system maintenance allows scales to be changed, traces to be added or removed, and colors to be changed. In addition, the display is interactive, so that selecting a region of the graph allows access to the raw data for that section. This happens in such a way that returning to the summary view is simple (perhaps bringing up a separate window for the raw data, for example).

3) Review/Perform ECG Analysis

Once the user selects a patient case, if the ECG analysis has not already been performed at the time of data download, the user is asked to confirm if ECG analysis should be performed immediately. The entire patient session is sent to the ECG analyzer 98, and the progress through analysis is reported to the user by way of a progress bar. Once completed, the results of the analysis are saved to the session record. The analysis options outlined in the following use cases are presented to the user. By default the summary report should be shown when analysis is complete.

The user is offered the ability to display a histogram of R-R intervals in the analyzed data. Also, a template display is provided which displays a page with the top 12 beat types, including the number of each type and the percent of total beats. The beats shown are one actual beat from the raw data, including its time. The user is permitted to navigate forwards and backwards through the different occurrences of that beat type in the raw data. The user may go to the section of data corresponding to a given beat; such a display is in the "full disclosure" format where a trace is displayed with the same basic properties as the raw data graphs. Additionally, the ECG trace is labeled with all classified beats and rhythms identified by the ECG analyzer 98. A summary report of the results of ECG analysis is generated. The user has simple access to print out a report. On the other hand, the ST/QT/VEB graph of ST Level, QT Interval, and VEB frequency and heart rate, plotted against time for the entire session may be available.

4) Review Auxiliary Data

This routine displays a graph of data acquired from the auxiliary sensors at the base station unit 30. If no data exists for one of the auxiliary sensor types, no axes are drawn for that sensor. Graphs plotted are blood pressure (with systolic, diastolic and mean plotted on the same set of axes), FEV1 and PEF (highest of three readings plotted on different axes) and weight. All data points for a given series are joined by lines. Time base range is selectable between 1 week, 1 month, 3 months and 6 months.

Review Events

Figure 10:
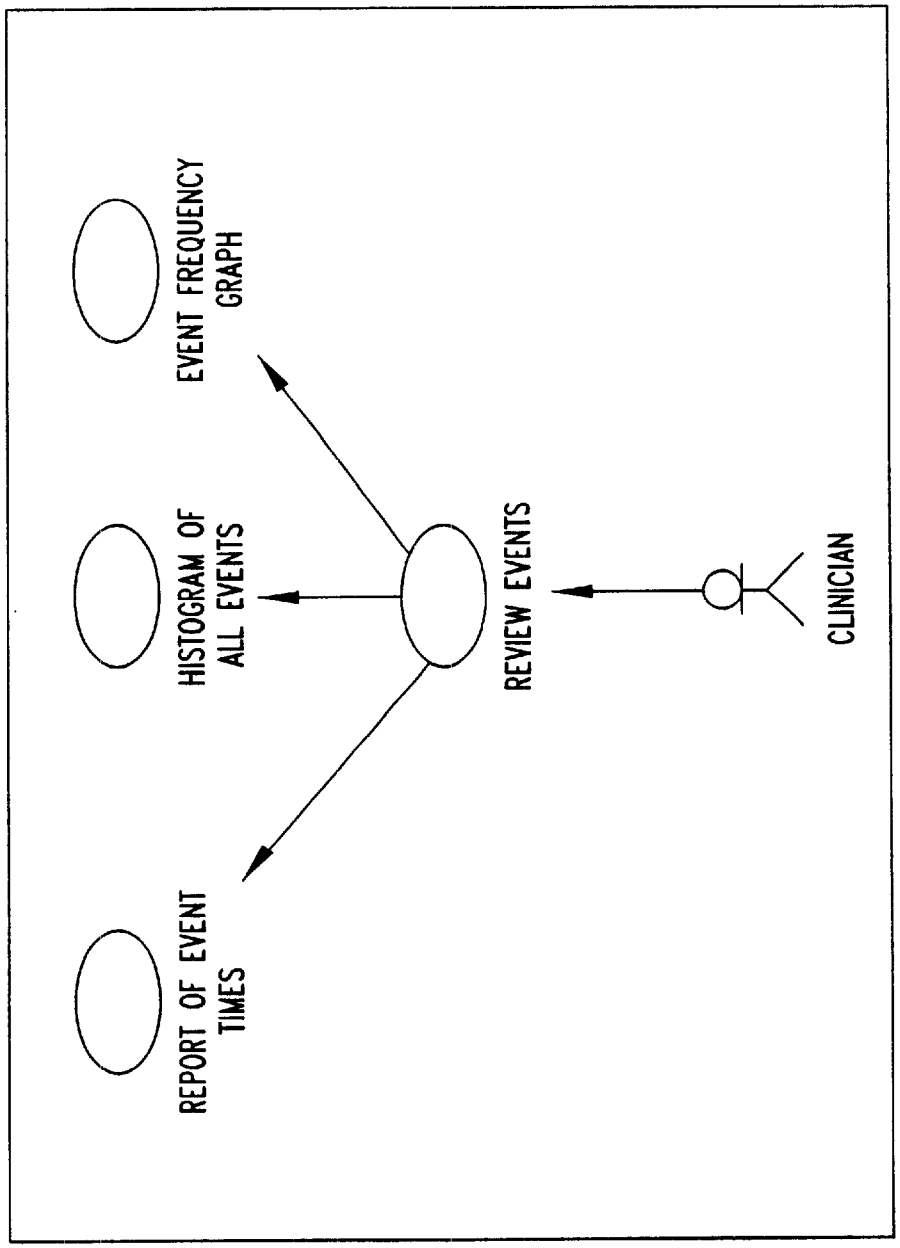
FIG. 10 illustrates the "review events" process implemented by the monitoring station of the invention.

Specific event analysis is always performed on an event for a single patient. The user is asked the time period during which to review an event. The default is the last 7 days. FIG. 10 illustrates an analysis of the applicable alarms.

1) Report of Event Times

This report is the simplest and lists, in a text based form, the events that have occurred in the specified period. Information listed includes the time the event was triggered, the type of event, and the cause of the event (e.g. high threshold triggered). The only customization is the ability to selectively show event of a particular type or all events. The default is to show all events.

From a given event, it is possible to go to the data associated with it. For certain events, the data will have automatically been downloaded with the event itself; for others, the data may be included in an already downloaded session. In the remaining case, where there is no data associated with an event, the user is prompted to download the associated data.

2) Histogram of all Events

This report shows a histogram spanning the selected time period, showing the number of events of each type that occurred. The histogram columns are determined by the events selected for the patient. Threshold events will give rise to 2 columns each, one for high trigger, the other for low trigger.

3) Event Frequency Graph

This report shows a graph plotting the total number of events per 15-minute interval against time. The graph is interactive in that selecting a point on the graph will open up a histogram, but with the data taken only from the selected 15-minute period.

C. Use of Remote Monitoring Station Software

Use of the remote monitoring station software will now be described with respect to the user interface screen displays of FIGS. 11 and 12.

To use the remote monitoring station software, the user logs in by entering a valid user name and password into a log in screen. Unless the user is a technician desiring to perform system maintenance, the user also ensures that the option "I want to monitor patient data" is selected. Once logged in, the user selects a patient using a choose patient screen. A patient can be found by using the patient number, study code, patient initials, or any combination of these by entering the data and selecting a "Find" button. If the user desires to see a list of all patients, the user selects a "Select from all patients" button. On the other hand, if the user wishes to work with a new patient who has no record in the system, the user selects an "Add new patient" button. If no patients meet the search criteria, the user will be given a warning message. If the search resulted in just one patient, then the patient information will be shown in the "Case Home Screen" described below. However, if the search resulted in more than one patient, then the user will be shown a list of patients. The user selects the desired patient from the list and clicks on a "View selected patient" button. If the desired patient is not in the list, the user may select a "Go Back" button to try another search.

Figure 11A:
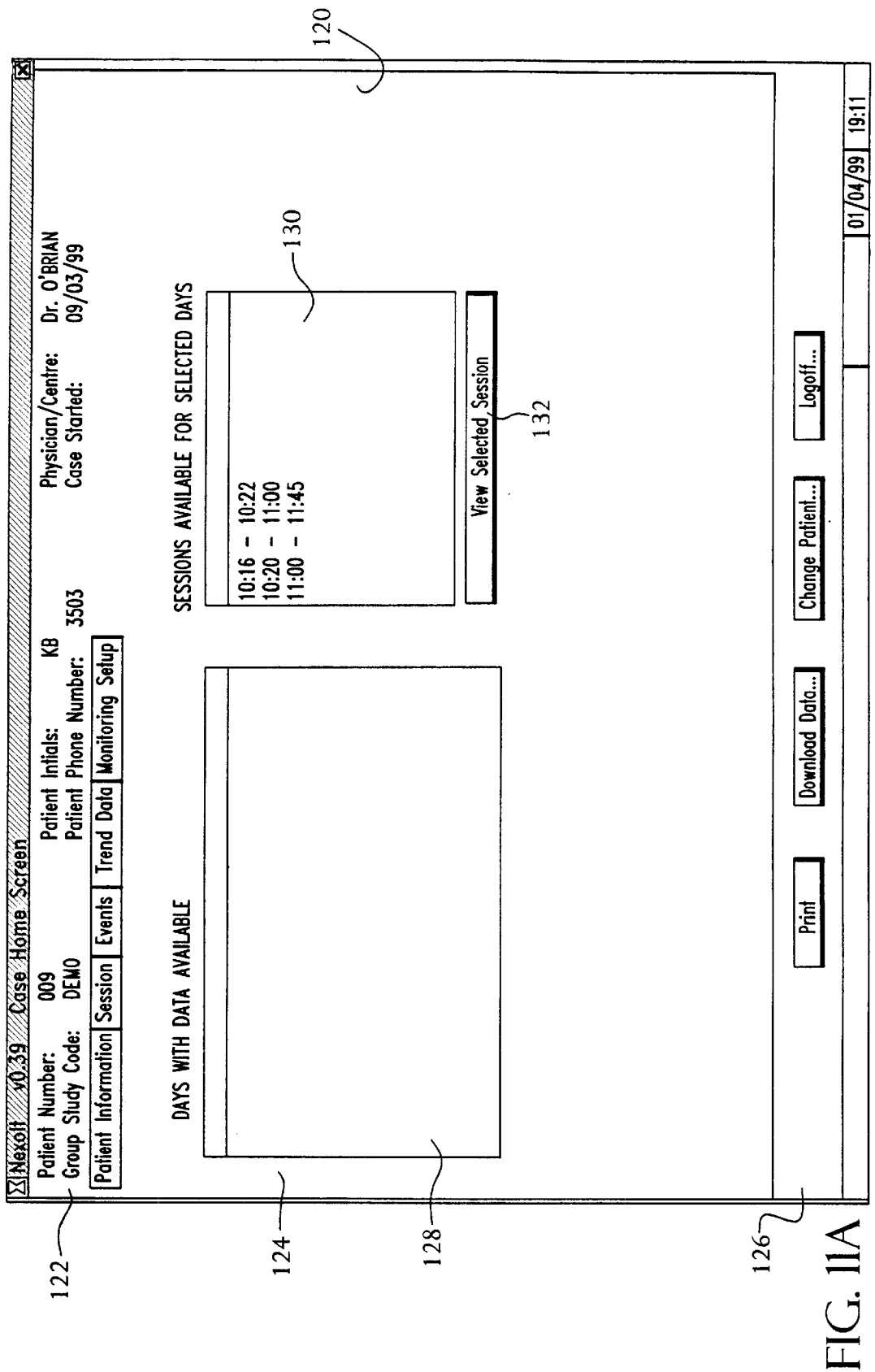
FIG. 11A illustrates the case home screen with the sessions available for the selected patient.

Once a patient has been selected, the patient's data is loaded into the case home screen 120 illustrated in FIG. 11A. As shown, the case home screen 120 is divided into three areas: a portion 122 providing information relating to the currently selected patient and study case, a portion 124 listing a number of tabs that allow the user to look at various different configurations as well as to select different sessions of data, and a portion 126 including buttons for allowing the user to print various screens, download the patient data, and to change the currently selected patient.

In order to navigate among the various options, the user selects one of the tabs in portion 122.

Upon selecting the "Sessions" tab, the user sees the boxes 128 and 130 of FIG. 11A. A list of days with sessions available is displayed in box 128, and a list of different times of the sessions is shown in box 130. The user selects a day from box 128 and one of the corresponding session times from box 130. The user then selects the "View selected session" button 132, and the session data is then loaded and displayed to the user.

Figure 11B:
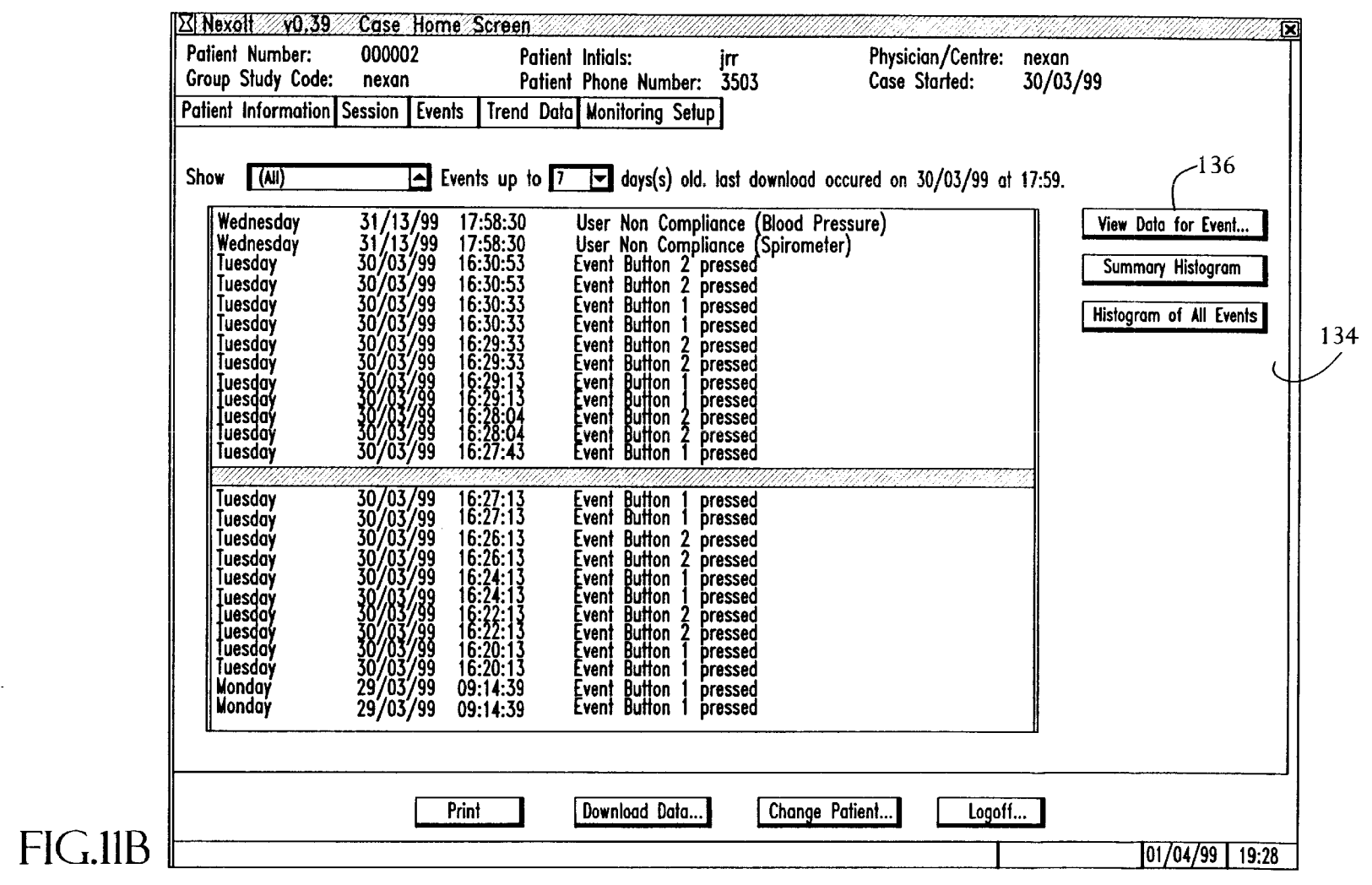

FIG. 11B illustrates the events screen 134 which appears when the "Events" tab is selected. As illustrated, the events screen 134 lists the events that have occurred over a period of time. The use may select what type of event is shown (or elect to show all events) and over what period of time the events are to be collected. The user also receives an indication of when the last download of patient data occurred. To view the monitored data associated with an event, the user selects the event from the list and selects the "View data for event" button 136. The data is then loaded and displayed to the user.

FIG. 11C illustrates the monitoring screen 138 which appears when the "Monitoring Setup" tab is selected. Monitoring screen 138 gives a number of configuration options which allow the user to change the way in which the selected patient is monitored. The top half of the monitoring screen 138 allows the user to change when and for how long the patient is monitored, including which days, the time of day, and for how long the patient will be monitored. The user may select up to 4 fixed times in which to monitor or elect to monitor on a periodic basis, such as every 6 hours. The next part of the monitoring screen 138 allows the user to configure the time of day that the application will automatically call the patient's base station unit 30 to download the patient data from the base station unit 30 to the remote monitoring station 50. The bottom part of screen 138 allows the user to setup which events should be monitored and the thresholds for these events. The user may also configure how much data on either side of the event should be downloaded in the next scheduled download.

As desired, electronic case record forms (CRFs) may also be generated directly from the data stored in the remote monitoring station 50 for each patient by CRF generating software, thereby greatly simplifying the reporting process for drug trials and the like. An electronic CRF would dictate a schedule for the patient's therapy via setup of the base station unit 30 by the remote monitoring station 50. The specified vital signs data could then be collected and inserted into the electronic CRF for management of a drug trial's results and submission of the results for FDA approval and the like, as necessary.

Figure 11D:
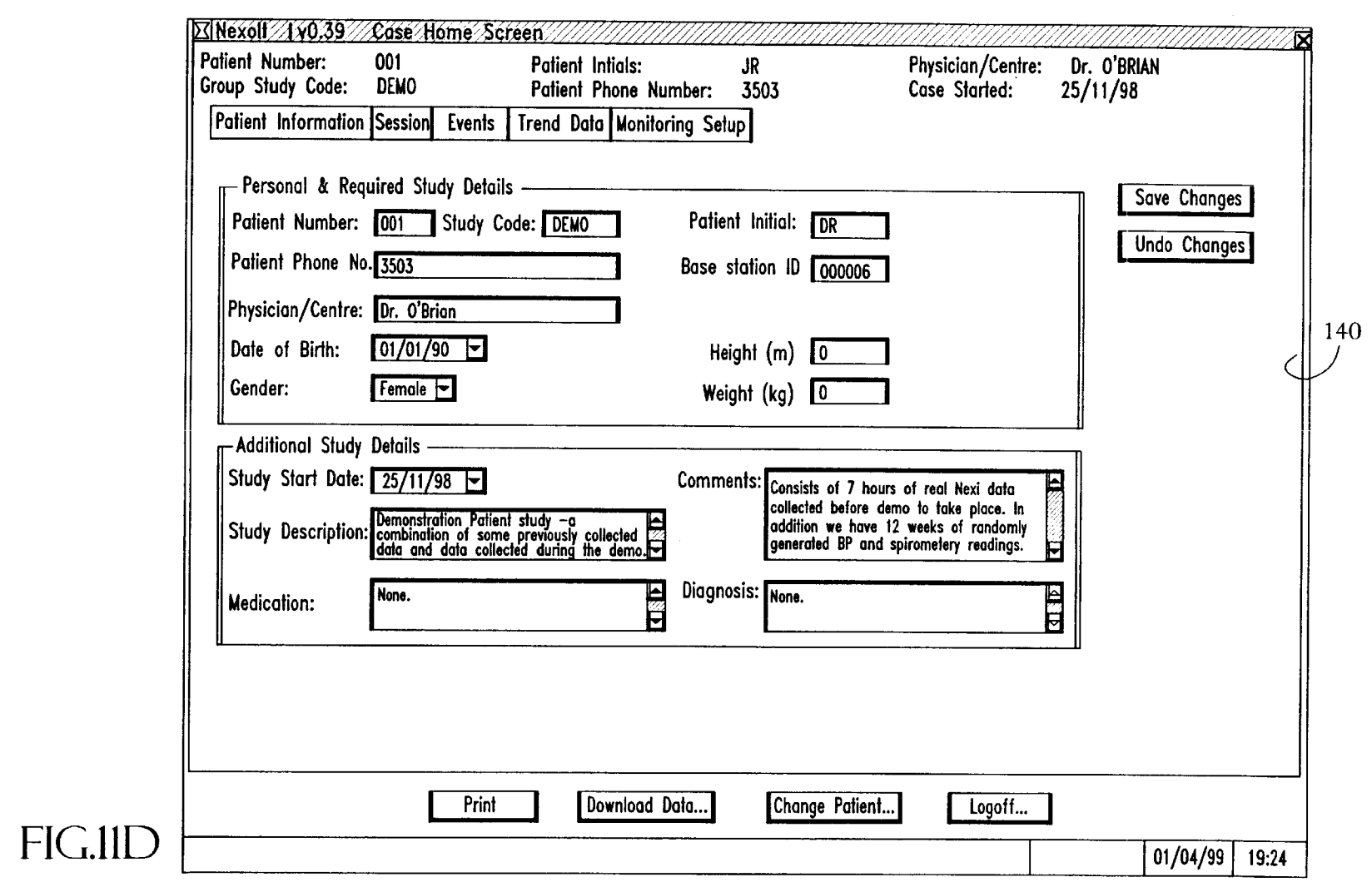

FIG. 11D illustrates the patient information screen 140 that appears when the "Patient Information" tab is selected. Patient information screen 140 displays all information relating to the patient and permits the patient information to be updated. The patient phone number is the telephone number that the application will use to call the base station unit for downloading the monitored data.

Figure 11E:
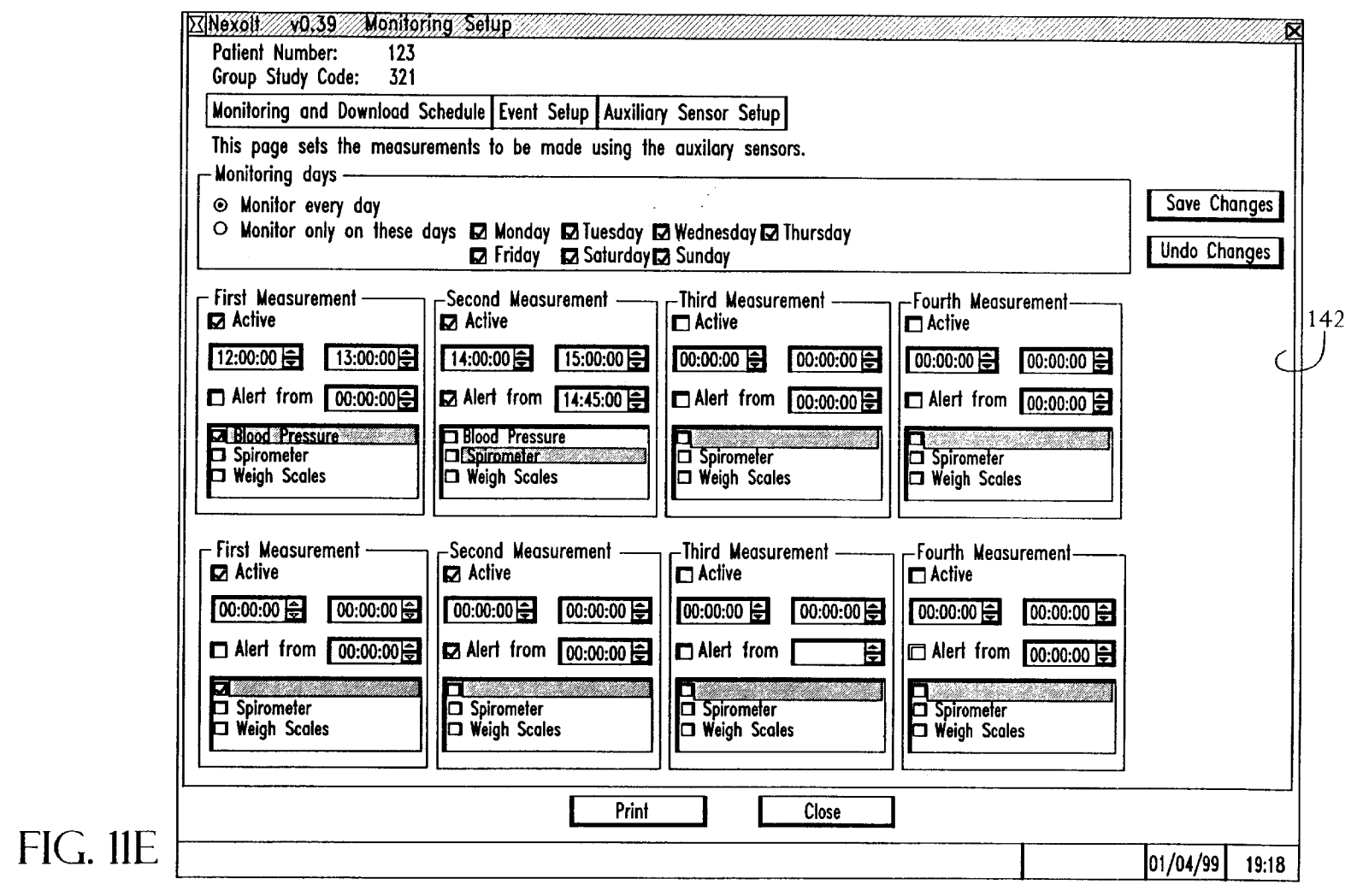

FIG. 11E illustrates the auxiliary sensors screen 142 that appears when the "Auxiliary Sensors" tab is selected. Auxiliary sensors screen 142 displays a number of configuration options that allow the user to change the way in which the auxiliary sensor measurements are taken at the base station unit 30. The top part of the auxiliary sensors screen 142 allows the user to setup on which days the auxiliary sensor measurements are taken, while the rest of the auxiliary sensors screen 142 allows the user to configure up to 8 different measurements to be taken each day. The user simply selects "Active" in the checkbox and then specifies the time period in which the measurement must be taken. The user may also tell the base station unit 30 to alert the patient by selecting the "Alert from" checkbox and specify the time at which this alert should take place. As noted above, the alert may be a light and buzzer on the base station unit 30. Finally, the user selects the type of measurement from the list of available auxiliary sensors (e.g. blood pressure) to be used during the measurement.

Figure 11F:
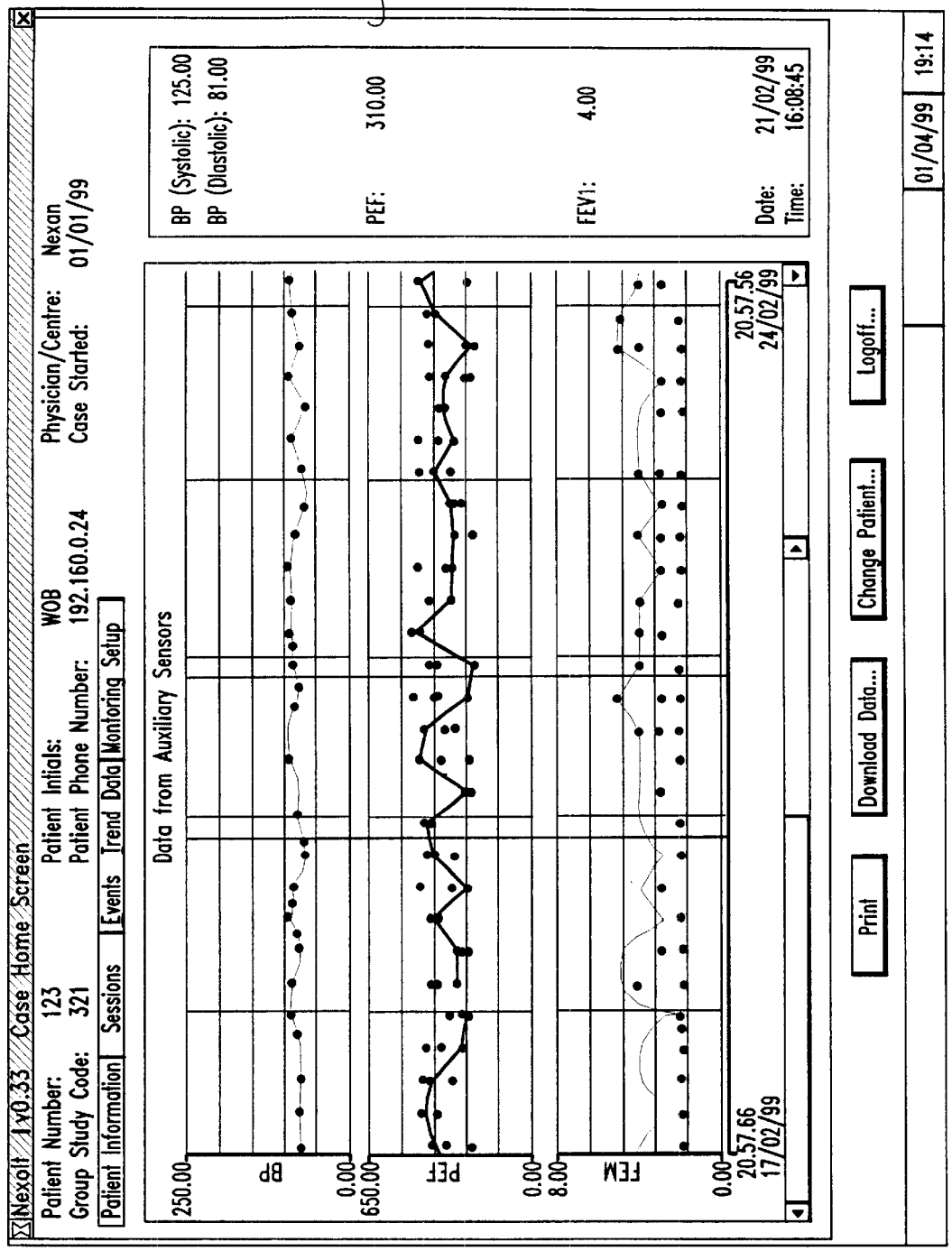
FIG. 11F illustrates the trend data screen for displaying auxiliary sensor data available for the selected patient.

FIG. 11F illustrates the trend data screen 144 that appears when the "Trend Data" tab is selected. Trend data screen 144 displays the readings taken from the auxiliary sensors during the study case. The layout varies depending on which auxiliary sensors are in use for a given patient.

As illustrated in FIGS. 11A–11F, the user is given the option of printing a report for the currently selected tab, to download data immediately from the base station unit 30, to change patients, or to exit.

Figure 12:
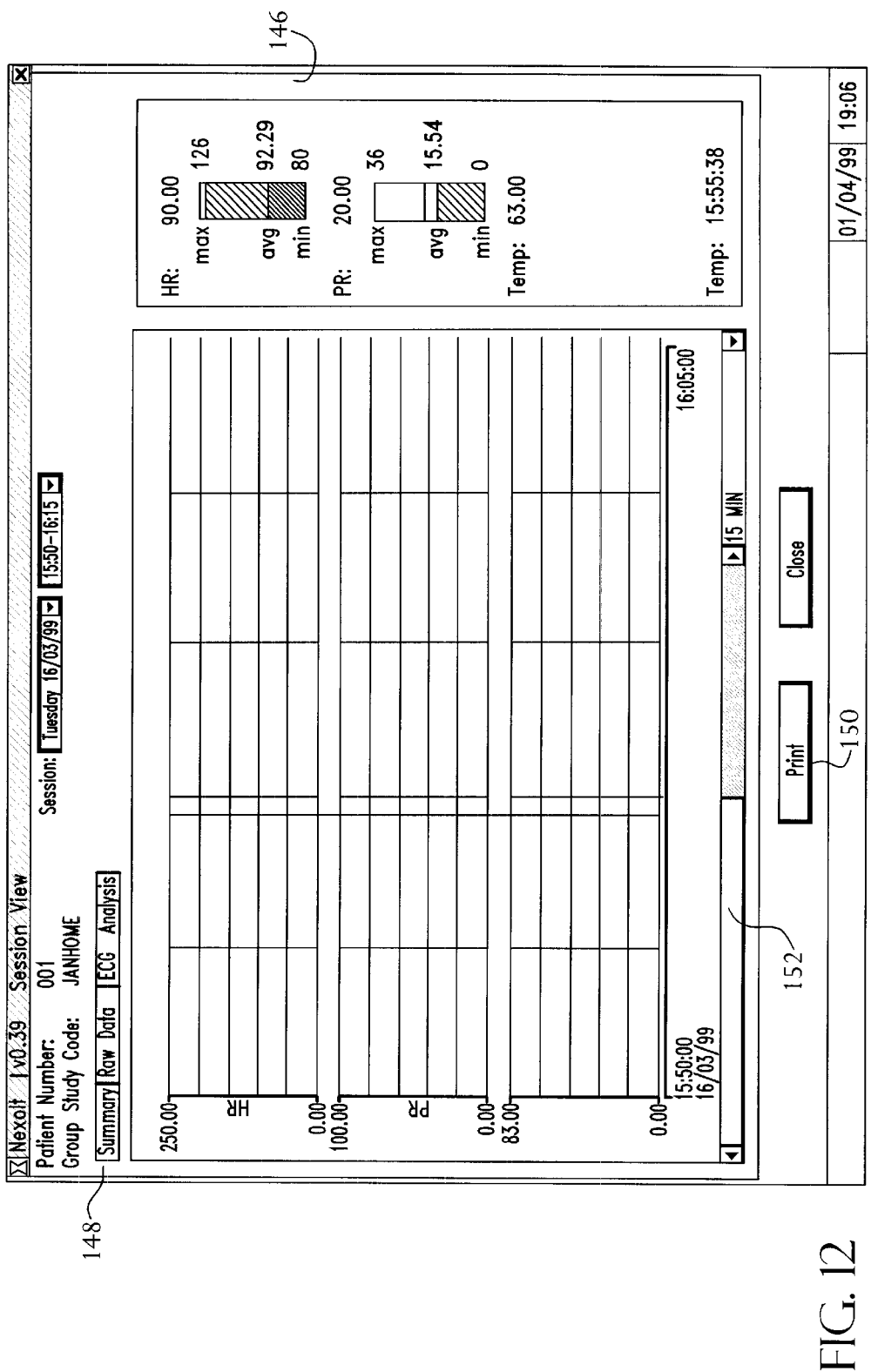
FIG. 12 illustrates the summary graphs for heart rate, respiration and temperature when the summary button is selected.

When the user has selected a patient session to view from the case home screen 120, the session data is loaded into a session view screen 146 of the type illustrated in FIG. 12. As illustrated in FIG. 12, the session view screen 146 provides session information and allows the user to change the session to be viewed, provides a set of tabs 148 from which to select to view either raw, summary or ECG data, and provides buttons 150 to allow the user to print various screens and to close the session view screen 146.

FIG. 12 illustrates the summary graphs for heart rate, respiration and temperature when the summary button is selected and provides a way for the user to look at the data over a larger range of time (i.e., hours instead of minutes). Scroll bar 152 allows the user to move the cursor along the graph and to view the graph at different time scales. On the other hand, the user may manipulate the cursor with a mouse to move the cursor along the graph. Scroll bar 152 also allows the user to view the graphs at different times. Also, the user may select the "Raw Data" tab to review raw data over a smaller range of time or select the "ECG Analysis" tab to view the ECG analysis data for the current session. The user may select from among the types of ECG analysis available, and the system will display the analysis report.

Remote, electronic capture of multiple and continuous vital signs data in accordance with the invention has the following benefits:

1. Reduction in study costs by replacing expensive clinic visit measurement with domiciliary data capture.

2. Reduction in the number of patients, study time and/or clinic visits required in drug trials through the availability of repeat data, offered by repeat at-home monitoring.

3. Increased safety and improved follow-up of patients provided by domiciliary monitoring.

4. Better management of patients with chronic diseases, with continuous or semi-continuous monitoring, enabling therapy regimes to be refined on an individual basis and possibly preventing acute episodes or deterioration.

5. Increased volumes of patient data for more informed patient diagnoses.

6. The capability to simultaneously capture multiple vital signs data, for example, blood pressure and ECG as defined by study or treatment protocol.

7. The ability to develop predictive algorithms to facilitate more effective treatment protocols by monitoring continuous parameters and comparing patterns with those collected from collections of other patients with similar conditions.

8. Greater speed and simplicity in data handling provided by electronic data capture.

9. Simple, easy-to-use technology (cordless, non-obtrusive design, ideal for night-time monitoring).

In short, the present invention provides more data, earlier, and at a lower cost than current telemonitoring systems. In addition, the ability to monitor the patient continuously for several days means that parameters such as duration of drug effect, drug-drug interactions and safety, which are difficult to measure/monitor at present, may now be measured in a domiciliary setting thereby optimizing drug or other therapies. In particular, the system of the invention permits closed loop control of drug presentation to the patient, whereby the physician may directly monitor the effects of adjusting drug dosages. Also, the system is designed to be very user-friendly, both from the patient's and the physician's perspectives, offering substantial advantages in patient compliance as compared to current telemetric monitoring methods. Though the use of a memory card 20 or smart card 20' without transmission circuitry in accordance with the invention is not conducive to real-time monitoring, the use of a memory/smart card 20 is particularly well suited to non-real-time monitoring as when monitoring the effects of a new medication on a patient, monitoring the progress of disease in a patient over time, and the like. For real-time monitoring, a system similar to that described in the parent application, U.S. patent application Ser. No. 09/292,405 would be preferred.

Although an exemplary embodiment of the invention has been described in detail above, those skilled in the art will readily appreciate that many additional modifications are possible in the exemplary embodiment without materially departing from the novel teachings and advantages of the invention. For example, data processing such as ECG analysis could be performed at the base station unit 30 and only the summary data transmitted to the remote monitoring station 50, thereby reducing download times considerably. Also, software may be provided to the patient for use in downloading software and uploading data from/to an Internet server for connection to a predetermined remote monitoring station connected to a designated node on the Internet. This approach would eliminate the need for (and cost of) a separate base station. If auxiliary sensor functions were still required, connections could be built into the hardware of the patient's personal computer. All such modifications are intended to be included within the scope of this invention as defined in the following claims.

What is claimed is:

1. A health parameter data collection and monitoring system, comprising:
   a smart card which stores said health parameter data;
   a sensor band having a sensor assembly for application to a subject, said sensor assembly sensing health parameter data indicative of values of at least one health parameter of the subject, said sensor band further comprising a connector which accepts said smart card, said smart card comprising a memory and a microprocessor operable to drive said sensor assembly, receive signals comprising said health parameter data from said sensor assembly, and store said health parameter data in said memory; and
   a monitoring station including a smart card reader which is adapted to read said health parameter data from said smart card.

2. A system as in claim 1, wherein said monitoring station comprises a base station unit connected to a remote monitoring station via a communications link, said base station unit including said smart card reader and a memory which stores health parameter data read from said smart card until at least one of said health parameter data and a summary of said health parameter data is transmitted to said remote monitoring station via said communications link.

3. A system as in claim 2, wherein said remote monitoring station requests transmission of health parameter data stored in said base station unit at predetermined times or conditions or on demand.

4. A system as in claim 3, wherein said remote monitoring station includes an interface which allows a user to set said predetermined times or conditions for said transmission of said health parameter data to said remote monitoring station.

5. A system as in claim 4, wherein said interface allows the user of the remote monitoring station to select a subject for review of at least that subject's health parameter data.

6. A system as in claim 4, wherein said interface allows the user to simultaneously review and compare time synchronized health parameter data for a plurality of health parameters for a particular subject.

7. A system as in claim 4, wherein said interface permits the user to select at least one of unprocessed health parameter data and summary data for display to the user of the remote monitoring station.

8. A system as in claim 1, further comprising a database accessible by said monitoring station to store health parameter data for a plurality of subjects.

9. A system as in claim 8, wherein said monitoring station includes software which generates case record forms from at least the health parameter data stored for a subject in said database.

10. A system as in claim 1, wherein said sensor band is adapted for attachment to a chest of the subject and said sensor assembly senses health parameter data indicative of at least one of ECG, respiration, skin temperature, $SpO_2$ and subject motion.

11. A system as in claim 10, wherein said sensor band comprises a plurality of ECG sensor electrodes.

12. A system as in claim 11, wherein said sensor band further comprises an optional sensor band connector for accepting at least an additional ECG sensor electrode.

13. A system as in claim 10, wherein said smart card is adapted to store at least 24 hours' worth of said health parameter data.

14. A system as in claim 10, wherein said sensor band comprises signal processing circuitry that processes said health parameter data for storage on said smart card.

15. A system as in claim 14, wherein said smart card further comprises FM signal transmission circuitry, said system further comprising a data logger in range of said signal transmission circuitry so as to receive and store transmitted health parameter data for a period of time until said health parameter data may be downloaded to said monitoring station.

16. A system as in claim 15, wherein at least one of said smart card and said data logger comprises data compression circuitry that compresses received health parameter data.

17. A system as in claim 15, wherein said FM signal transmission circuitry inserts an identifier that identifies at least one of said smart card and said sensor band as the source of the transmitted health parameter data.

18. A system as in claim 10, wherein said smart card comprises signal processing circuitry for processing said signals comprising health parameter data.

19. A system as in claim 18, wherein said smart card further comprises FM signal transmission circuitry, said system further comprising a data logger in range of said signal transmission circuitry so as to receive and store transmitted health parameter for a period of time until said health parameter data may be downloaded to said monitoring station.

20. A system as in claim 19, wherein at least one of said smart card and said data logger comprises data compression circuitry that compresses received health parameter data.

21. A system as in claim 19, wherein said FM signal transmission circuitry inserts an identifier that identifies at least one of said smart card and said sensor band as the source of the transmitted health parameter data.

22. A system as in claim 1, wherein said connector comprises a battery, said battery providing electrical energy to said sensor band.

23. A system as in claim 1, wherein said smart card is rechargeable.

24. The system as in claim 1, wherein said smart card is adapted to receive health parameter data from at least a second sensing device.

25. The system as in claim 24, wherein said at least a second sensing device is adapted to collect health parameter data indicative of at least one of $SpO_2$, blood pressure, temperature, and subject motion.

26. A health parameter data collection and monitoring system, comprising:
   a smart card which stores said health parameter data;
   a sensor band having a sensor assembly for application to a subject, said sensor assembly sensing health parameter data indicative of values of at least one health parameter of the subject, said sensor band further comprising a connector which accepts said smart card, said smart card comprising a memory and a microprocessor operable to drive said sensor assembly, receive signals comprising said health parameter data from said sensor assembly, and store said health parameter data in said memory;

a base station unit including a smart card reader and a memory which stores health parameter data read from said smart card; and a remote monitoring station connected to said base station unit via a communications link, said remote monitoring station uploading, via said communications link, health parameter data stored in said memory of said base station unit.

27. A system as in claim 26, wherein said base station unit includes a processor which calculates physiological parameter data including at least one of a subject's heart rate and a subject's respiration rate from said health parameter data and stores a summary of said physiological parameter data in said memory for transmission to said remote monitoring station.

28. A system as in claim 26, wherein said memory of said base station unit is a rolling first-in-first-out (FIFO) memory which stores said health parameter data irrespective of whether said health parameter data has been transmitted to said remote monitoring station.

29. A system as in claim 26, wherein said base station unit comprises at least one input connection for accepting auxiliary data input from an auxiliary health parameter sensor and said memory stores said auxiliary data input for transmission to said remote monitoring station.

30. A system as in claim 29, wherein said at least one input connection is operable for accepting auxiliary data from a plurality of devices, and said base station unit is operable to identify which of said plurality of devices is connected to said at least one input connection at any given time.

31. A system as in claim 29, wherein said base station unit time stamps said health parameter data and said auxiliary data and manages independently said auxiliary data and said health parameter data while stored in said memory of said base station unit.

32. A system as in claim 29, wherein said auxiliary health parameter sensor is at least one of a blood pressure sensor, a spirometer, a weigh scale, an oximeter, and a blood glucose meter.

33. A system as in claim 29, wherein said base station unit detects abnormal physiological conditions in said auxiliary data and indicates an event condition and stores event data indicating a significant physiological event in said memory when an abnormal physiological condition is detected.

34. A system as in claim 33, wherein said base station unit time stamps said health parameter data, said auxiliary data, and event data and manages independently said auxiliary data and said health parameter data while stored in said memory of said base station unit.

35. A system as in claim 29, wherein said base station unit includes a processor which calculates physiological auxiliary parameter data from said auxiliary data and stores a summary of said physiological auxiliary parameter data in said memory at said base station unit for transmission to said remote monitoring station.

36. A system as in claim 35, wherein said processor further performs ECG analysis of said health parameter data and stores ECG analysis data in said memory.

37. A system as in claim 35, wherein said memory separately stores said health parameter data and said calculated physiological auxiliary parameter data.

38. A system as in claim 35, wherein said remote monitoring station comprises a monitoring station processor and a monitoring station memory, said monitoring station processor performing ECG analysis of said health parameter data and stores ECG analysis data in said monitoring station memory.

39. A system as in claim 35, wherein said remote monitoring station comprises a monitoring station processor and a monitoring station memory, said monitoring station processor performing respiratory rate analysis of said health parameter data and stores respiratory rate analysis data in said monitoring station memory.

40. A system as in claim 35, wherein said remote monitoring station comprises a monitoring station processor and a monitoring station memory, said monitoring station processor performing $SpO_2$ analysis of said health parameter data and stores $SpO_2$ analysis data in said monitoring station memory.

41. A system as in claim 29, wherein said remote monitoring station includes an interface which allows a user to schedule auxiliary health parameter sensor measurements at said base station unit if such measurements are required.

42. A system as in claim 26, wherein said base station unit compares received health parameter data with predetermined ranges for detected physiological variables and detects abnormal physiological conditions in said health parameter data, said base station unit indicating an event condition and storing event data indicating a significant physiological event in said memory when said received health parameter data is outside said predetermined ranges or when an abnormal physiological condition is detected.

43. A system as in claim 42, wherein said memory of said base station unit is a rolling first-in-first-out (FIFO) memory which stores at least said health parameter data irrespective of whether said health parameter data has been transmitted to said remote monitoring station.

44. The system of claim 43, wherein said rolling first-in-first-out memory further stores event data irrespective of whether said event data has been transmitted to said remote monitoring station.

45. A system as in claim 42, wherein said remote monitoring station includes an interface which allows a user to set at least one of said predetermined ranges of said base station unit.

46. A system as in claim 42, wherein said remote monitoring station includes software which checks received data for event data and an interface which allows a user to view such event data, whereby if event data is detected, said interface allows the user of said remote monitoring station to view a desired amount of health parameter data before, during, and after an occurrence of an event condition indicated by said event data.

47. A system as in claim 26, wherein said communications link is a telecommunications link.

48. A system as in claim 47, wherein said remote monitoring station initiates a connection with said base station unit, and once the connection is established, said remote monitoring station and base station unit listen for commands.

49. A system as in claim 48, wherein said commands include a data request command from said remote monitoring station requesting health parameter data in a designated time range from said base station unit.

50. A system as in claim 26, wherein an ID of said base station unit is checked by said remote monitoring station before data is transmitted via said communications link.

51. A system as in claim 26, further comprising a database accessible by said remote monitoring station to capture and store health parameter data for a plurality of subjects and said remote monitoring station further includes an interface through which a user of the remote monitoring station may select a subject for review of at least that subject's health parameter data.

52. The system of claim 51, wherein said interface is operable to maintain an audit trail of actions performed by the user when using said interface and of actions performed by said remote monitoring station.

53. A system as in claim 26, wherein said remote monitoring station is adapted to receive health parameter data transmitted by at least two base station units.

54. A system as in claim 53, wherein said remote monitoring station includes a server which controls the receipt and storage of health parameter data from said at least two base station units.

55. A health parameter data collection and monitoring system, comprising:
    an insertable card including an FM signal transmitter;
    a sensor band having a sensor assembly for application to a subject, said sensor assembly sensing health parameter data indicative of values of at least one health parameter of the subject, said sensor band further comprising a connector which accepts said insertable card, said insertable card operable to receive said health parameter data from said sensor assembly and transmit said health parameter data using said FM signal transmitter; and
    a remote monitoring station including a radio module which is adapted to receive transmitted health parameter data from said insertable card and to store said health parameter data in a database.

56. A system as in claim 55, further comprising a portable data logger that receives transmitted health parameter data from said insertable card and stores said health parameter data until said data logger may download the received health parameter data to said remote monitoring station.

57. A system as in claim 56, wherein said sensor band comprises signal processing circuitry that processes said health parameter data for transmission to said portable data logger.

58. A system as in claim 56, wherein said insertable card comprises signal processing circuitry that processes said health parameter data for transmission to said portable data logger.

59. A method of collecting health parameter data, comprising the steps of:
    providing a sensor band for application to a subject, said sensor band having a sensor assembly that produces health parameter data indicative of values of at least one health parameter of the subject;
    providing a smart card for insertion into a connector of said sensor band, said smart card comprising a memory and a microprocessor operable to drive said sensor assembly, receive signals comprising said health parameter data from said sensor assembly, and store said health parameter data in said memory; and
    providing a monitoring station including a smart card reader which is adapted to read said health parameter data from said smart card for storage in a database.

60. A method as in claim 59, wherein said monitoring station comprises a base station unit connected to a remote monitoring station via a communications link, said method comprising the additional step of storing said health parameter data in said base station unit until a designated time for transmission of said health parameter data to said remote monitoring station via said communications link.

61. A method of claim 59, wherein said monitoring station comprises a base station unit connected to a remote monitoring station via a communications link, said method comprising the additional step of storing said health parameter data in said base station unit until at least one of said health parameter data and a summary of said health parameter data is transmitted to said remote monitoring station via said communications link.

62. A method as in claim 60, comprising the additional step of transmitting said health parameter data to said remote monitoring station at said designated time, in response to a certain condition, or on demand.

63. A method as in claim 62, comprising the further step of allowing a user to set said designated time and certain condition for said transmission of said health parameter data to said remote monitoring station.

64. A method as in claim 63, comprising the further step of accessing said health parameter data stored in said database for medical diagnosis or analysis.

65. A method as in claim 64, wherein said step of accessing said health parameter data comprises the step of using the remote monitoring station to select a subject for review of at least that subject's health parameter data.

66. A method as in claim 65, wherein said step of accessing said health parameter data comprises the step of simultaneously reviewing and comparing time synchronized health parameter data for a plurality of health parameters for the selected subject.

67. A method as in claim 64, wherein said step of accessing said health parameter data step comprises the step of permitting the user to select at least one of unprocessed health parameter data and summary data for display.

68. A method as in claim 64, comprising the further step of generating case record forms from at least the health parameter data stored for a subject in said database.

69. A method as in claim 59, comprising the further steps of determining whether the subject moved during a measurement of said health parameter data and deleting or ignoring health parameter data collected during a time the subject moved if such movement may have corrupted the health parameter data.

70. A method as in claim 69, wherein corruption of the health parameter data is determined by comparing motion data to at least one of an ECG waveform and a respiration waveform.

71. A method of collecting health parameter data, comprising the steps of:
    providing a sensor band for application to a subject, said sensor band having a sensor assembly that produces health parameter data indicative of values of at least one health parameter of the subject;
    providing a smart card for insertion into a connector of said sensor band, said smart card adapted receive said health parameter data from said sensor assembly and to transmit said health parameter data from said sensor assembly; and
    providing a monitoring station including a receiver which is adapted to receive said transmitted health parameter data from said smart card for storage in a database.

72. A method as in claim 71, wherein said smart card comprises FM signal transmission circuitry, said method comprising the further steps of providing a data logger in range of said signal transmission circuitry so as to receive and store transmitted health parameter for a period of time until said health parameter data may be downloaded to said monitoring station.

73. A method as in claim 71, comprising the further step of compressing said transmitted health parameter data prior to transmission and storage.

74. A method as in claim 71, comprising the additional step of transmitting an identifier with said health parameter data that identifies at least one of said smart card and said sensor band as the source of the transmitted health parameter data.

75. A method of collecting health parameter data, comprising the steps of:

providing a sensor band for application to a subject, said sensor band having a sensor assembly that produces health parameter data indicative of values of at least one health parameter of the subject;

providing an insertable card including an FM signal transmitter for insertion into a connector of said sensor band, said insertable card adapted to receive said health parameter data from said sensor assembly and transmit said health parameter data from said sensor assembly; and providing a monitoring station including a receiver which is adapted to receive said transmitted health parameter data from said insertable card for storage in a database.

76. A method of continuously monitoring a subject's health parameters during a drug/therapy trial, comprising the steps of:

applying a sensor band having a sensor assembly to a subject whereby said sensor assembly produces health parameter data indicative of values of at least one health parameter of the subjects;

providing a drug/therapy to the subject and electronically providing event data indicating that the drug/therapy has been provided and when;

inserting a smart card into said sensor band, said smart card comprising a memory and a microprocessor operable to drive said sensor assembly, receive signals comprising said health parameter data from said sensor assembly, and store said health parameter data in said memory;

removing said smart card after a predetermined period of time; and inserting said removed smart card into a remote monitoring station that captures said health parameter data and said event data for storage in a database as a continuous record of the subject's health parameters during a trial period of said drug/therapy, whereby said subject's physiological condition during said trial period may be monitored remotely.

77. A method as in claim 76, comprising the further step of electronically providing event data marking (1) that the subject feels ill and (2) when the subject feels ill.

78. A method as in claim 77, comprising the further step of collecting health parameter data at times before, during, and after the timing of an event marked by said event data and providing a display of any changes in said health parameter data as a result of said drug/therapy or of the subject feeling ill.

* * * * *

UNITED STATES PATENT AND TRADEMARK OFFICE
CERTIFICATE OF CORRECTION

PATENT NO. : 6,454,708 B1
DATED : September 24, 2002
INVENTOR(S) : Pete Ferguson et al.

It is certified that error appears in the above-identified patent and that said Letters Patent is hereby corrected as shown below:

Column 1,
Line 38, delete "base" and insert -- based -- therefor;

Column 3,
Line 25, delete "aprecordial" and insert -- a precordial -- therefor;

Column 19,
Line 51, delete "100" and insert -- 110 -- therefor;

Column 20,
Line 66, insert -- . -- after "110";

Column 24,
Line 6, delete "10" and insert -- 110 -- therefor;

Column 34,
Line 51, insert -- to -- after "adapted".

Signed and Sealed this

Fourth Day of January, 2005

JON W. DUDAS
*Director of the United States Patent and Trademark Office*